US009606057B2

(12) United States Patent
Kapelushnik et al.

(10) Patent No.: US 9,606,057 B2
(45) Date of Patent: Mar. 28, 2017

(54) BIOCHEMICAL ANALYSIS OF PBMC

(75) Inventors: Joseph Kapelushnik, Moshav Neve Ilan (IL); Shaul Mordechai, Omer (IL); Ilana Nathan, Omer (IL); Udi Zelig, Kibbutz Nir Yitzhak (IL); Rami Zigdon, Ra'anana (IL)

(73) Assignee: TODOS MEDICAL LTD., Airport (IL)

( * ) Notice: Subject to any disclaimer, the term of this patent is extended or adjusted under 35 U.S.C. 154(b) by 0 days.

(21) Appl. No.: 13/701,262

(22) PCT Filed: Jun. 1, 2011

(86) PCT No.: PCT/IL2011/000426
§ 371 (c)(1),
(2), (4) Date: Feb. 12, 2013

(87) PCT Pub. No.: WO2011/151825
PCT Pub. Date: Dec. 8, 2011

(65) Prior Publication Data
US 2013/0143258 A1    Jun. 6, 2013

Related U.S. Application Data

(60) Provisional application No. 61/350,073, filed on Jun. 1, 2010.

(51) Int. Cl.
G01N 33/48    (2006.01)
C12Q 1/04    (2006.01)
G01N 21/63    (2006.01)
G01J 3/433    (2006.01)
G01N 21/35    (2014.01)
G01N 21/3563    (2014.01)

(52) U.S. Cl.
CPC .............. *G01N 21/63* (2013.01); *G01J 3/433* (2013.01); *G01N 21/35* (2013.01); *G01N 21/3563* (2013.01); *G01N 2021/3595* (2013.01)

(58) Field of Classification Search
CPC .... G01N 21/63; G01N 21/35; G01N 21/3563; G01N 2021/3595; G01J 3/433
USPC ............................................. 435/34; 356/39
See application file for complete search history.

(56) References Cited

U.S. PATENT DOCUMENTS

| | | | |
|---|---|---|---|
| 4,832,483 A | 5/1989 | Verma | |
| 4,912,050 A | 3/1990 | Fossel | |
| 5,197,470 A | 3/1993 | Helfer et al. | |
| 5,261,410 A | 11/1993 | Alfano et al. | |
| 5,697,373 A | 12/1997 | Richards-Kortum et al. | |
| 5,733,739 A | 3/1998 | Zakim et al. | |
| 5,734,587 A | 3/1998 | Backhaus et al. | |
| 5,945,675 A | 8/1999 | Malins | |
| 6,251,616 B1 | 6/2001 | Barbera-Guillem | |
| 6,274,871 B1* | 8/2001 | Dukor et al. | 250/339.08 |
| 6,642,012 B1* | 11/2003 | Ashdown | 435/7.24 |
| 6,841,388 B2 | 1/2005 | Dukor et al. | |
| 7,524,681 B2 | 4/2009 | Wolf et al. | |
| 7,611,839 B2 | 11/2009 | Twine | |
| 8,173,433 B2 | 5/2012 | Folkman et al. | |
| 2001/0000150 A1 | 4/2001 | Malins | |
| 2004/0073011 A1 | 4/2004 | Hagay et al. | |
| 2004/0110221 A1 | 6/2004 | Twine et al. | |
| 2004/0186383 A1* | 9/2004 | Rava et al. | 600/473 |
| 2005/0017179 A1 | 1/2005 | Mordechai et al. | |
| 2006/0194211 A1 | 8/2006 | Burczynski | |
| 2007/0003921 A1 | 1/2007 | Andrus | |
| 2009/0004682 A1 | 1/2009 | Kitamura et al. | |
| 2009/0175819 A1 | 7/2009 | Priest et al. | |
| 2010/0021039 A1 | 1/2010 | Ortyn et al. | |
| 2010/0185064 A1 | 7/2010 | Bandic et al. | |
| 2010/0210023 A1 | 8/2010 | Wong et al. | |
| 2010/0273191 A1 | 10/2010 | Arber | |
| 2011/0028808 A1 | 2/2011 | Kuratsune et al. | |
| 2011/0182881 A1 | 7/2011 | Chin et al. | |
| 2013/0137134 A1 | 5/2013 | Mordechai | |
| 2014/0087397 A1 | 3/2014 | Romick-Rosendale et al. | |

FOREIGN PATENT DOCUMENTS

| | | |
|---|---|---|
| WO | 2009/074988 | 6/2009 |
| WO | 2011/121588 | 10/2011 |
| WO | 2011/151825 | 12/2011 |
| WO | 2012/153326 | 11/2012 |

OTHER PUBLICATIONS

Wood et al. Fourier Transform Infrared Spectroscopy As a Method for Monitoring the Molecular Dynamics of Lymphocyte Activation; Applied Spectroscopy, vol. 54, No. 3 (2000) pp. 353-359.*
Gao et al. Human Breast Carcinomal Tissues Display Distinctive FTIR Spectra: Implication for the Histological Chracterization of Carcinomas; Analytical Cellular Pathology, vol. 18 (1999) pp. 87-93.*
Bitar et al. Biochemical Analysis of Human Breast Tissues Using Fourier-Transform Raman Spectroscopy; Journal of Biomedical Optics, vol. 11, No. 5 (2006) pp. 1-8.*
U.S. Appl. No. 61/350,073, filed Jun. 1, 2010.
An International Search Report and a Written Opinion both dated Nov. 29, 2011, which issued during the prosecution of Applicant's PCT/IL2011/000426.
An International Search Report and a Written Opinion both dated Aug. 3, 2011, which issued during the prosecution of Applicant's PCT/IL2011/000282.
An International Search Report and a Written Opinion both dated Aug. 31, 2012, which issued during the prosecution of Applicant's PCT/IL2012/000187.

(Continued)

*Primary Examiner* — Scott Long
*Assistant Examiner* — Paul Martin
(74) *Attorney, Agent, or Firm* — Sughrue Mion, PLLC

(57) ABSTRACT

A method is provided comprising, obtaining an infrared (IR) spectrum of a Peripheral Blood Mononuclear Cells (PBMC) sample by analyzing the sample by infrared spectroscopy; and based on the infrared spectrum, generating an output indicative of the presence of a solid tumor or a pre-malignant condition. Other embodiments are also provided.

9 Claims, 13 Drawing Sheets

(56) References Cited

OTHER PUBLICATIONS

An International Preliminary Report on Patentability dated Nov. 12, 2013, which issued during the prosecution of Applicant's PCT/IL2012/000187.

Agatha G., et al., Fatty acid composition of lymphocyte membrane phospholipids in children with acute leukemia. Cancer Lett. Nov. 28, 2001;173(2):139-44.

Arakawa H., et al., Silver (I) complexes with DNA and RNA studied by Fourier transform infrared spectroscopy and capillary electrophoresis. Biophys J. Sep. 2001;81(3):1580-7.

Argov S., et al., Diagnostic potential of Fourier-transform infrared microspectroscopy and advanced computational methods in colon cancer patients. J Biomed Opt. Apr. 2002;7(2):248-54.

Argov S, Sahu RK, Bernshtain E, Salman A, Shohat G, Zelig U, Mordechai S. Inflammatory bowel diseases as an intermediate stage between normal and cancer: a FTIR-microspectroscopy approach.

Backhaus J., et al., Diagnosis of breast cancer with infrared spectroscopy from serum sample. Vibrational Spectroscopy 52(2010) 173-177.

Beyer M., and Schulze J. L., Regulatory T cells in cancer. Blood. Aug. 1, 2006;108(3):804-11.

Bogomolny E., et al., Early spectral changes of cellular malignant transformation using Fourier transformation infrared microspectroscopy. 2007. J Biomed Opt.12:024003.

Boydston-White ST., et al., 1999, Infrared spectroscopy of human tissue V infrared spectroscopic studies of myeloid leukemia (ML-1) cells at different phases of cell cycle. Biospectroscopy 5:219-227.

Coates RJ, et al., Diagnostic markers for ovarian cancer screening: not ready for routine clinical use. Clin Cancer Res. Nov. 15, 2008;14(22):7575-6.

Curiel TJ., et al., Specific recruitment of regulatory T cells in ovarian carcinoma fosters immune privilege and predicts reduced survival. Nat Med. Sep. 2004;10(9):942-9.

Diem M., et al., A decade of Vibrational micro-spectroscopy of human cells and tissue (1994-2004). Analyst 129,88-885 (2004).

Duffy MJ. Role of tumor markers in patients with solid cancers: A critical review. Eur J Intern Med. May 2007;18(3):175-184.

Fabian H., et al., Diagnosing benign and malignant lesions in breast tissue sections by using IR-microspectroscopy. Biochim Biophys Acta. Jul. 2006;1758(7):874-82.

Gazi E., et al., Biomolecular profiling of metastatic prostate cancer cells in bone marrow tissue using FTIR microspectroscopy: a pilot study. Anal Bioanal Chem. Mar. 2007;387(5):1621-31.

Gottfried EL., Lipids of human leukocytes: relation to celltype. J Lipid Res. Jul. 1967;8(4):321-7.

Graser A., et al., Comparison of CT colonography, colonoscopy, sigmoidoscopy and faecal occult blood tests for the detection of advanced adenoma in an average risk population. Gut. Feb. 2009;58(2):241-8.

Handy B. The Clinical Utility of Tumor Markers. LabMedicine. Feb. 2009; 40, 99-103.

Hammody Z., et al., Distinction of malignant melanoma and epidermis using IR micro-spectroscopy and statistical methods. Analyst. Mar. 2008;133(3):372-8.

Hildebrand J., et al., Neutral glycolipids in leukemic and nonleukemic leukocytes. J Lipid Res. May 1971;12(3):361-6.

Inbar M., et al., Cholesterol as a bioregulator in the development and inhibition of leukemia. Proc Natl Acad Sci U S A. Oct. 1974;71(10):4229-31.

Inbar M., et al., Fluidity difference of membrane lipids in human normal and leukemic lymphocytes as controlled by serum components. Cancer Res. Sep. 1977;37(9):3037-41.

Kanika Singh., et al., Spectroscopic techniques as a diagnostic tool for early detection of osteoporosis. Journal of Mechanical Science and Technology vol. 24, No. 8, 1661-1668.

Khanmohammadi M., et al., Diagnosis of basal cell carcinoma by infrared spectroscopy of whole blood samples applying soft independent modeling class analogy. J Cancer Res Clin Oncol. Dec. 2007;133(12):1001-10. Epub Aug. 2, 2007.

Kiviniemi MT., et al., Decision making about cancer screening: an assessment of the state of the science and a suggested research agenda from the ASPO Behavioral Oncology and Cancer Communication Special Interest Group. Cancer Epidemiol Biomarkers Prev. Nov. 2009;18(11):3133-7.

Krafft C., et al., Identification of primary tumors of brain metastases by SIMCA classification of IR spectroscopic images. Biochim Biophys Acta. Jul. 2006;1758(7):883-91.

Kriat M., et al., Analysis of plasma lipids by NMR spectroscopy: application to modifications induced by malignant tumors. J Lipid Res. Jun. 1993;34(6):1009-19.

Leong PP., et al., Phenotyping of lymphocytes expressing regulatory and effector markers in infiltrating ductal carcinoma of the breast. Immunol Lett. Feb. 15, 2006;102(2):229-36.

Liu KZ., et al., Bimolecular characterization of leucocytes by infrared spectroscopy. Br J Haematol. Mar. 2007;136 (5):713-22.

Liu Z., et al., Tumor regulatory T cells potently abrogate antitumor immunity. J Immunol. May 15, 2009;182(10):6160-7.

Liyanage UK., et al., Prevalence of regulatory T cells is increased in peripheral blood and tumor microenvironment of patients with pancreas or breast adenocarcinoma. J Immunol. Sep. 1, 2002;169(5):2756-61.

Lyman DJ., et al., Fourier transform infrared attenuated total reflection analysis of human hair: comparison of hair from breast cancer patients with hair from healthy subjects. *Appl. Spectrosc.* Jan. 2005;59(1):26-32.

Mitchell PS., et al., Circulating microRNAs as stable blood-based markers for cancer detection. PNAS Jul. 29, 2008 vol. 105 No. 30 10513-10518.

Cazzaniga G, Biondi A. Molecular monitoring of childhood acute lymphoblastic leukemia using antigen receptor gene rearrangements and quantitative polymerase chain reaction technology. Haematologica. Mar. 2005;90(3):382-90.

Mordechai S., et al., Possible common biomarkers from FTIR microspectroscopy of cervical cancer and melanoma. J Microsc. Jul. 2004;215(Pt 1):86-91.

Naumann D. FT-infrared and FT-Raman spectroscopy in bio-medical research, Appl. Spectrosc. Rev. 36, 239-298 (2001).

Pavlou MP, Diamandis EP. The cancer cell secretome: a good source for discovering biomarkers? J Proteomics. Sep. 10, 2010;73(10):1896-906.

Petibois C., et al., Plasma protein contents determined by Fourier-transform infrared spectrometry. Clin Chem. Apr. 2001;47(4):730-8.

Petibois C., et al., Analytical performances of FT-IR spectrometry and imaging for concentration measurements within biological fluids, cells, and tissues. Analyst. May 2006;131(5):640-7.

Campana D. Molecular determinants of treatment response in acute lymphoblastic leukemia. Hematology Am Soc Hematol Educ Program. 2008:366-73.

Petter CH., et al., Development and application of Fourier-transform infrared chemical imaging of tumour in human tissue. Curr Med Chem. 2009;16(3):318-26.

Ransohoff DF. Rules of evidence for cancer molecular-marker discovery and validation. Nat Rev Cancer. Apr. 2004;4(4):309-14.

Sahu RK., et al., Detection of abnormal proliferation in histologically 'normal' colonic biopsies using FTIR-microspectroscopy. Scand J Gastroenterol. Jun. 2004;39(6):557-66.

Sahu RK., et al., Can Fourier transform infrared spectroscopy at higher wavenumbers (mid IR) shed light on biomarkers for carcinogenesis in tissues? J Biomed Opt. Sep.-Oct. 2005;10(5):054017.

Sahu RK., et al., Continuous monitoring of WBC (biochemistry) in an adult leukemia patient using advanced FTIR-spectroscopy. Leuk Res. Jun. 2006;30(6):687-93.

Sasada T., et al., CD4+CD25+ regulatory T cells in patients with gastrointestinal malignancies: possible involvement of regulatory T cells in disease progression. Cancer. Sep. 1, 2003;98(5):1089-99.

Saslow D., et al., American Cancer Society Breast Cancer Advisory Group. American Cancer Society guidelines for breast screening with MRI as an adjunct to mammography. CA Cancer J Clin. Mar.-Apr. 2007;57(2):75-89. Erratum in: CA Cancer J Clin. May-Jun. 2007;57(3):185.

(56) References Cited

OTHER PUBLICATIONS

Shaw RA., et al., Multianalyte serum analysis using mid-infrared spectroscopy. Ann Clin Biochem. Sep. 1998;35 ( Pt 5):624-32.
Shimokawara I., et al., Identification of lymphocyte subpopulations in human breast cancer tissue and its significance: an immunoperoxidase study with antihuman T- and B-cell sera. Cancer. Apr. 1, 1982;49(7):1456-64.
Smith RA., et al., Cancer screening in the United States, 2010: a review of current American Cancer Society guidelines and issues in cancer screening. CA Cancer J Clin. Mar.-Apr. 2010;60(2):99-119.
Spiegel, R J., et al., 1982. Plasma lipids alterations in leukemia and lymphoma. Am. J. Med. 72: 775-781.
Tokuno K., et al., Increased prevalence of regulatory T-cells in the peripheral blood of patients with gastrointestinal cancer. Anticancer Res. May 2009;29(5):1527-32.
Toyran N., et al., Selenium alters the lipid content and protein profile of rat heart: an FTIR microspectroscopy study. Arch. Biochem.Biophys. 2007 458:184-193.
Whitehead RH., et al., T and B lymphocytes in breast cancer stage relationship and abrogation of T-lymphocyte depression by enzyme treatment in vitro. Lancet. Feb. 14, 1976;1(7955):330-3.
Whitford P., et al., Flow cytometric analysis of tumour infiltrating lymphocytes in breast cancer. Br J Cancer. Dec. 1990;62(6):971-5.
Wieczorek G., et al., Quantitative DNA methylation analysis of FOXP3 as a new method for counting regulatory T cells in peripheral blood and solid tissue. Cancer Res. Jan. 15, 2009;69(2):599-608.
Wolf AM., et al., Increase of regulatory T cells in the peripheral blood of cancer patients. Clin Cancer Res. Feb. 2003;9(2):606-12.
Zelig U., et al., Diagnosis of cell death by means of infrared spectroscopy. Biophys J Oct. 7, 2009;79:2107-14.
Zhang SL, et al., Vibrational Spectra and Experimental Assignments of Thymine and Nine of its Isotopomers J. Phys. Chem. A. 102 (1998), p. 461.
An Office Action dated Aug. 19, 2013, which issued during the prosecution of U.S. Appl. No. 13/638,367.
Ramesh et al. Novel Methodology for the Follow-Up of Acute Lympblastic Leukemia Using FTIR Microspectroscopy; Journal of Biochemical and Biophysical Methods, vol. 51 (2002) pp. 251-261.
Mohlenhoff et al. Mie-Type Scattering and Non-Beer-Lambert absorption behavior of human cells in infrared microspectroscopy.
Bogomolny et al. "Monitoring of viral cancer progression using FTIR microscopy: A comparative study of intact cells and tissues."
Visintin, Irene, et al.: "Diagnostic Markers for Early Detection of Ovarian Cancer", Clin Cancer Res 2008; 14:1065-1072, DOI:10.1158/1078-0432.CCR-07-1569, Published online Feb. 7, 2008.
Hengartner, M. O. The biochemistry of apoptosis. Nature. 2000, 407: 770-776.
Andrus PG. Cancer monitoring by FTIR spectroscopy. Technol Cancer Res Treat. Apr. 2006;5(2):157-67.
Lavie Y, et al., Changes in membrane microdomains and caveolae constituents in multidrug-resistant cancer cells. Lipids. 1999;34 Suppl:S57-63.
Vrooman LM, Silverman LB. Childhood acute lymphoblastic leukemia: update on prognostic factors. Curr Opin Pediatr. Feb. 2009;21(1):1-8.
Krishna CM., et al., Combined Fourier transform infrared and Raman spectroscopic approach for identification of multidrug resistance phenotype in cancer cell lines. Biopolymers. Aug. 5, 2006;82(5):462-70.
Basso G, et al., Risk of relapse of childhood acute lymphoblastic leukemia is predicted by flow cytometric measurement of residual disease on day 15 bone marrow. J Clin Oncol. Nov. 1, 2009;27(31):5168-74.
Pui CH, Evans WE. Treatment of acute lymphoblastic leukemia. N Engl J Med 2006; 354: 166-78.
Tucci F, Aricò M. Treatment of pediatric acute lymphoblastic leukemia. Haematologica. Aug. 2008;93(8):1124-8.
Castillo L. A Randomized Trial of the I-BFM-SG for the Management of Childhood non-B Acute Lymphoblastic Leukemia. ALL IC-BFM 2002.
U.S. Appl. No. 61/318,395, filed Mar. 29, 2010.
Smith M, et al., Uniform approach to risk classification and treatment assignment for children with acutelymphoblastic leukemia. J Clin Oncol. Jan. 1996;14(1):18-24. PubMed PMID: 8558195.
Khanmohammadi et al., Chemometrics assisted investigation of variations in infrared spectra of blood samples obtained from women with breast cancer: a new approach for cancer diagnosis, Eur J Cancer Care, 2010, vol. 19, pp. 352 to 359.
Schultz et al., Study of Chronic Lymphocytic Leukemia Cells by FT-IR Spectroscopy and Cluster Analysis, Pergamon, Leukemia Research, 1996, vol. 20, No. 8, pp. 649 to 655.
Khanmohammadi et al., Cancer Diagnosis by Discrimination between Normal and Malignant Human Blood Samples Using Attenuated Total Reflectance-Fourier Transform Infrared Spectroscopy, Informa HealthCare, Cancer Investigation, 2007, vol. 25, pp. 397 to 404.
Communication dated Oct. 10, 2014, issued by the European Patent Office in corresponding European Application No. 12782256.7.
International Search Report with Written Opinion dated Apr. 23, 2014, issued by the International Searching Authority in corresponding International Application No. PCT/IL13/50945.
An English translation of a communication, issued by the Russian Patent Office in corresponding Russian Application No. 2012157998.
An English translation of RU 2 352 256.
Mehrotra et al., Analysis of ovarian tumor pathology by Fourier Transform Infrared Spectroscopy, Journal of Ovarian Research, 2010, vol. 3, No. 27, p. 1-6.
Devi et al., FTIR Spectroscopic Analysis of Normal and Cancerous Human Breast Tissues between 450 Cm-1 and 1100 Cm-1 using Trend Analysis, International Journal of ChemTech Research, Sep. 2010, vol. 2, No. 3, pp. 1426 to 1433.
Big Medicine Encyclopedia. Ed. Petrovskiy, vol. 12, 1980, 13 pages total.
Krishna et al, Characterisation of uterine sarcoma cell lines exhibiting MDR phenotype by vibrational spectroscopy, Biochimica et Biophysica Acta (BBA), Elsevier, 2005, General Subjects vol. 1726, Issue 2, pp. 160 to 167.
Bosschaart et al., "A literature review and novel theoretical approach on the optical properties of whole blood", Lasers Med Sci, 2014, vol. 29, pp. 453-479.
Meinke et al., "Optical propertied of platelets and blood plasma and their influence on the optical behavior of whole blood in the visible to near infrared wavelength range", J Biomed Opt, Jan.-Feb. 2007, vol. 12, No. 1, pp. 014024.
Communication dated Jun. 8, 2015, issued by the U.S. Patent and Trademark Office in corresponding U.S. Appl. No. 14/116,506.
Communication dated Feb. 12, 2016, issued by the United States Patent and Trademark Office in U.S. Appl. No. 14/116,506.

* cited by examiner

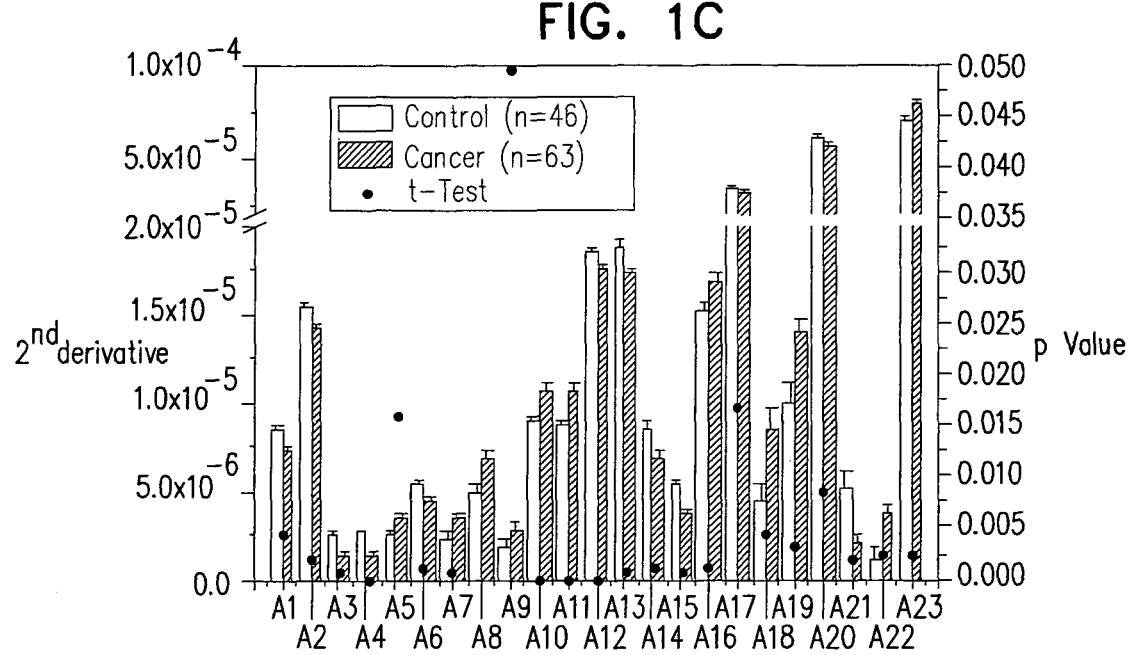

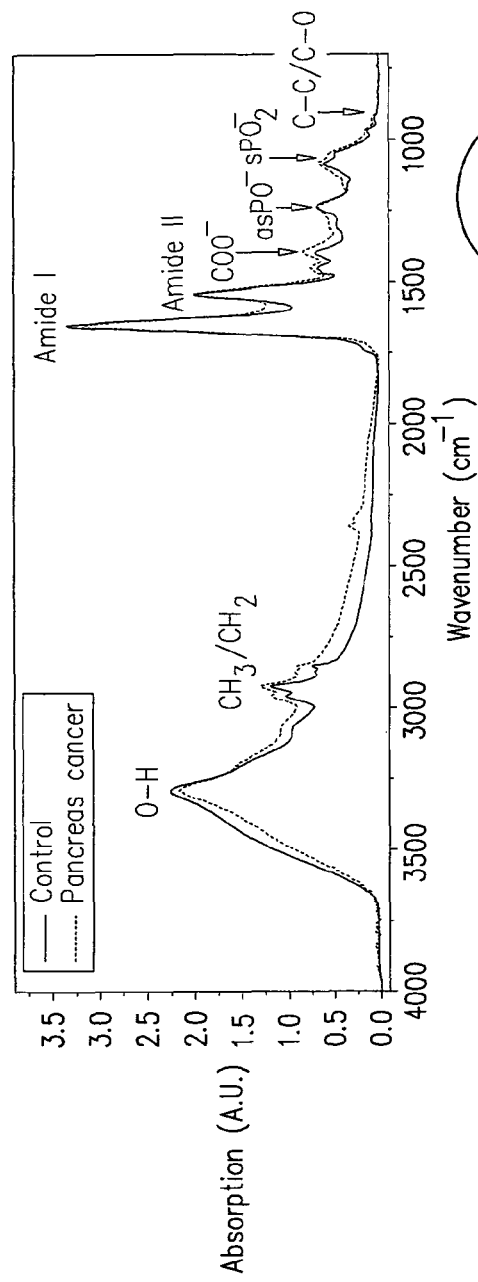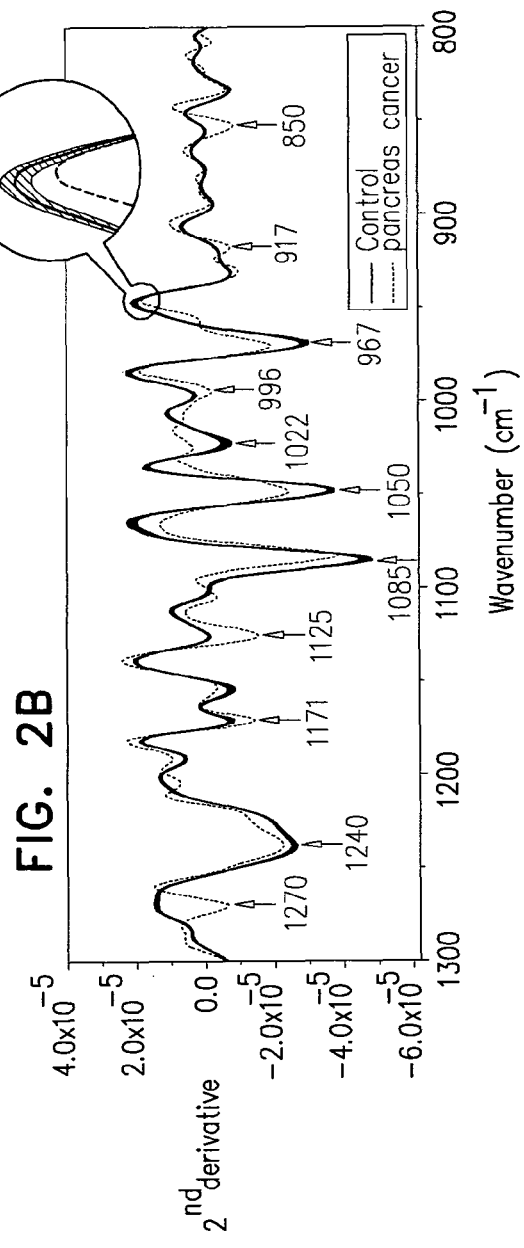
FIG. 2A
FIG. 2B

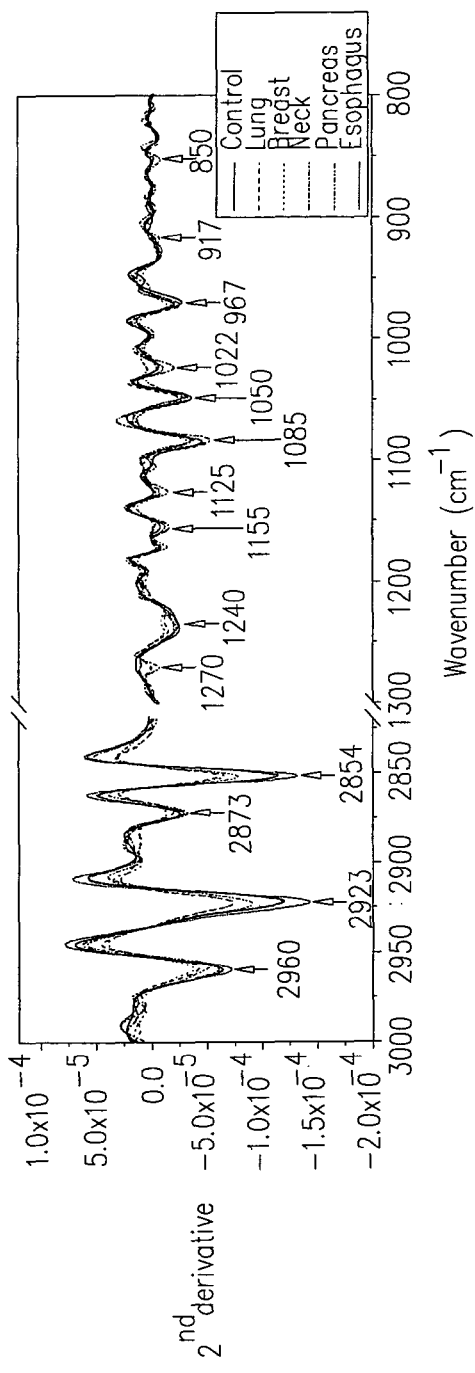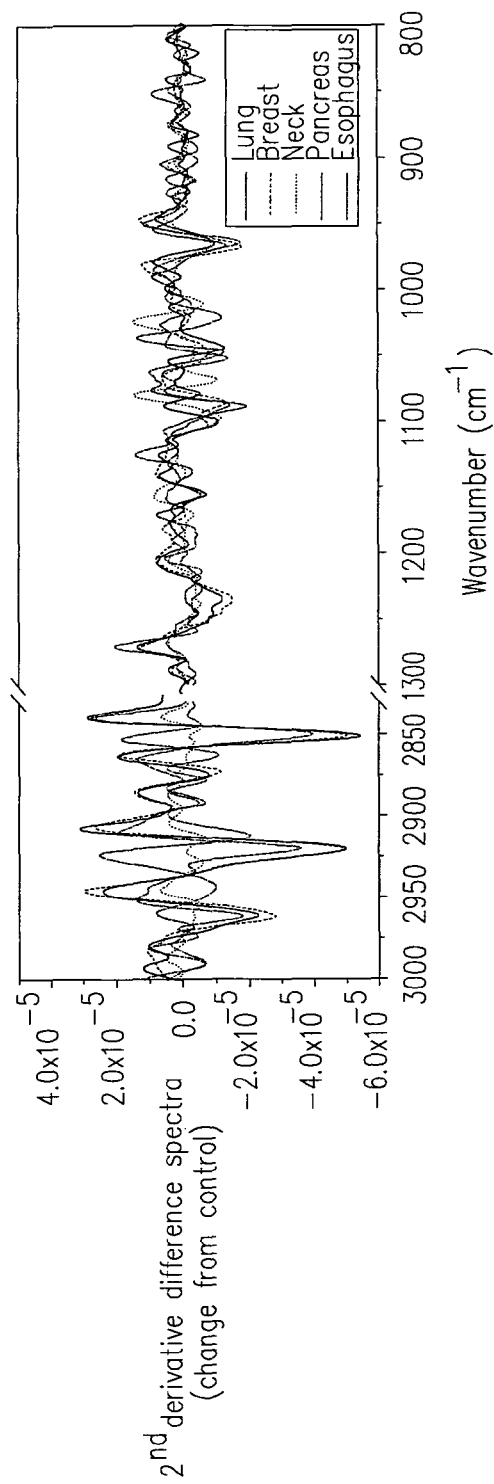
FIG. 3A
FIG. 3B

FIG. 3C

| Wavenumber (cm$^{-1}$) | Breast Cancer | Lung Cancer | Head & Neck Cancer | Pancreas Cancer | Esophagus Cancer |
|---|---|---|---|---|---|
| 2871 | ↓ | ↓ | | | |
| 2850 | ↓ | ↓ | | ↓ | |
| 1390 | ↓ | ↓ | ↓ | | |
| 1369 | | ↓ | | | |
| 1354 | | | | ↑ | |
| 1346 | | ↓ | | ↑ | |
| 1317 | | ↑ | | ↓ | ↑ |
| 1311 | | ↑ | | | |
| 1286 | | | | | ↑ |
| 1271 | ↑ | ↑ | | ↑ | ↑ |
| 1240 | ↓ | ↓ | ↓ | | |
| 1223 | ↓ | ↓ | | | |
| 1173 | ↓ | | | ↑ | |
| 1155 | ↓ | ↓ | ↑ | | ↑ |
| 1126 | | ↑ | | ↑ | |
| 1101 | ↓ | ↓ | ↓ | ↓ | ↓ |
| 1086 | ↓ | | ↑ | ↓ | ↓ |
| 1049 | ↓ | | | | |
| 1047 | ↓ | | | ↓ | ↓ |
| 1024 | | | ↑ | ↓ | ↑ |
| 995 | ↓ | | | | |
| 970 | ↓ | ↑ | ↑ | ↑ | ↓ |
| 930 | | | | ↑ | |
| 925 | | | | | ↑ |
| 918 | | | ↓ | ↑ | |
| 893 | | ↑ | | | |
| 876 | | | ↑ | | |
| 852 | | | | ↑ | ↑ |
| 839 | | ↑ | | ↓ | ↓ |
| 822 | ↑ | | | ↑ | |
| 810 | | ↑ | | ↑ | |
| 795 | ↓ | | | | |
| 779 | ↓ | | ↓ | | ↓ |
| 740 | ↓ | ↓ | ↓ | | |

BIOCHEMICAL ANALYSIS OF PBMC

CROSS-REFERENCES TO RELATED APPLICATIONS

The present application is a U.S. national phase of PCT Application no. PCT/IL2011/000426 to Kapelushnik et al., filed Jun. 1, 2011, which published as WO 2011/151825 to Kapelushnik et al., which claims the priority of U.S. Provisional Application 61/350,073 to Kapelushnik et al., filed Jun. 1, 2010, which is incorporated herein by reference.

FIELD OF EMBODIMENTS OF THE INVENTION

Embodiments of the present invention relate generally to diagnosis and monitoring of cancer, and particularly to methods for diagnosis and monitoring of malignant solid tumors.

BACKGROUND

Infrared spectroscopy is a technique based on the absorption or reflection of infrared radiation by chemical substances; each chemical substance having unique absorption spectra. Fourier Transform Infrared (FTIR) spectroscopy is used to identify biochemical compounds and examine the biochemical composition of a biological sample. Typically, FTIR spectra are composed of absorption bands each corresponding to specific functional groups related to cellular components such as lipids, proteins, carbohydrates and nucleic acids. Processes such as carcinogenesis may trigger global changes in cancer cell biochemistry resulting in differences in the absorption spectra when analyzed by FTIR spectroscopy techniques. Therefore, FTIR spectroscopy is commonly used to distinguish between normal and abnormal tissue by analyzing the changes in absorption bands of macromolecules such as lipids, proteins, carbohydrates and nucleic acids. Additionally, FTIR spectroscopy may be utilized for evaluation of cell death mode, cell cycle progression and the degree of maturation of hematopoietic cells.

SUMMARY OF EMBODIMENTS OF THE INVENTION

In some applications of the present invention, methods and systems are provided for the diagnosis and monitoring of multiple types of malignant neoplasms, particularly malignant solid tumors.

Additionally or alternatively, some applications of the present invention comprise diagnosis and monitoring of a pre-malignant condition.

Typically "Total Biochemical Infrared Analysis" (TBIA) of blood-derived mononuclear cells is used to diagnose a solid tumor. For example, some applications of the present invention comprise analysis by infrared (IR) spectroscopy, e.g., FTIR spectroscopy and microspectroscopy, of global biochemical properties of blood-derived mononuclear cells for the detection of solid tumors. As provided by some applications of the present invention, FTIR Optical Diagnosis Technology (FODT) analysis of biochemical changes in a Peripheral Blood Mononuclear Cells (PBMC) sample of a patient can indicate the presence of a solid tumor and/or a pre-malignant condition.

For some applications, biochemical analysis of PBMC obtained from cancer patients and from control individuals who do not suffer from a malignant solid tumor, e.g., healthy controls, is conducted using FTIR microspectroscopy techniques. In accordance with some applications of the present invention, PBMC from a plurality of cancer patients each suffering from a solid tumor (e.g., in the breast, pancreas, lung, head and neck, prostate, ovary, and gastrointestinal tract) is analyzed by FTIR microspectroscopy techniques. Subsequently, the FTIR spectra (absorption and/or reflection) of the PBMC samples of the cancer patients are compared to the FTIR spectra of PBMC samples obtained from the controls.

The inventors have identified that the PBMC samples obtained from cancer patients suffering from a malignant solid tumor produce FTIR spectra that differ from those of the control individuals who do not suffer from a malignant solid tumor, allowing distinguishing between the cancer patients and controls. Thus, some applications of the present invention can be used to diagnose cancer patients suffering from various types of malignancies, particularly solid tumors. Importantly, the distinction by FTIR spectroscopy between controls and patients suffering from solid tumors is typically performed based on analysis of PBMC and not of the actual tumor cells.

For some applications, a data processor analyzes the IR spectrum, e.g., the FTIR spectrum, of the PBMC sample of a subject. Information from the data processor is typically fed into an output unit that generates a result indicative of the presence of a solid tumor and/or a pre-malignant condition, based on the infrared (IR) spectrum. Additionally, the data processor is typically configured to calculate a second derivative of the infrared (IR) spectrum of the PBMC sample and, based on the second derivative of the infrared (IR) spectrum, to generate an output indicative of the presence of a solid tumor.

Additionally, the inventors have identified that PBMC obtained from each cancer patient suffering from a solid tumor produced an FTIR spectrum having a unique spectral pattern which is characteristic of the type of malignancy, e.g., breast, lung, prostate or gastrointestinal, and distinct from spectra of other malignancy types.

For some applications, analysis by IR spectroscopy, e.g., FTIR spectroscopy, of the biochemistry of PBMC or any other blood-derived cells is used for the screening of large populations, aiding in the early detection of solid tumors. FTIR spectroscopy (and microspectroscopy) is typically a simple, reagent-free and rapid method suitable for use as a screening test for large populations. Early detection of cancer generally enables early intervention and treatment, contributing to a reduced mortality rate.

There is therefore provided in accordance with some applications of the present invention a method including:

obtaining an infrared (IR) spectrum of a Peripheral Blood Mononuclear Cells (PBMC) sample by analyzing the sample by infrared spectroscopy, and based on the infrared spectrum, generating an output indicative of the presence of a solid tumor or a pre-malignant condition.

For some applications, generating the output includes generating the output indicative of the presence of the solid tumor.

For some applications, analyzing the sample by infrared (IR) spectroscopy includes analyzing the sample by Fourier Transformed Infrared (FTIR) spectroscopy, and obtaining the infrared (IR) spectrum includes obtaining a Fourier Transformed Infrared (FTIR) spectrum.

For some applications, analyzing the sample by infrared (IR) spectroscopy includes analyzing the sample by Fourier Transformed Infrared microspectroscopy (FTIR-MSP).

For some applications, analyzing includes assessing a characteristic of the sample at at least one wavenumber selected from the group consisting of: 765±4 cm-1, 798±4 cm-1, 809±4 cm-1, 814±4 cm-1, 875±4 cm-1, 997±4 cm-1, 1001±4 cm-1, 1015±4 cm-1, 1103±4 cm-1, 1118±4 cm-1, 1162±4 cm-1, 1221±4 cm-1, 1270±4 cm-1, 1283±4 cm-1, 1295±4 cm-1, 1315±4 cm-1, 1341±4 cm-1, 1367±4 cm-1, 1392±4 cm-1, 1429±4 cm-1, 1440±4 cm-1, 1445±4 cm-1 and 1455±4 cm-1.

For some applications, analyzing includes assessing the characteristic at at least two wavenumbers selected from the group.

For some applications, analyzing includes assessing the characteristic at at least three wavenumbers selected from the group.

For some applications, assessing the characteristic includes analyzing a band of the IR spectrum surrounding at least one wavenumber selected from the group.

For some applications, analyzing the sample includes obtaining a second derivative of the infrared (IR) spectrum of the sample.

For some applications, the infrared (IR) spectrum includes an absorption spectrum, and obtaining the infrared (IR) spectrum includes obtaining the absorption spectrum.

For some applications, the infrared (IR) spectrum includes a reflection spectrum, and obtaining the infrared (IR) spectrum includes obtaining the reflection spectrum.

For some applications, generating the output includes indicating via the output whether the solid tumor is a first type of solid tumor or a second type of solid tumor.

For some applications, the solid tumor includes a solid tumor in tissue selected from the group consisting of: head and neck, esophagus, and pancreas, and generating the output includes generating an output indicative of the presence of a solid tumor in tissue selected from the group.

For some applications, the solid tumor includes a solid tumor in tissue selected from the group consisting of: breast, gastrointestinal tract, prostate, and lung, and generating the output includes generating an output indicative of the presence of a solid tumor in tissue selected from the group.

For some applications, analyzing includes assessing a characteristic of the sample at at least one wavenumber selected from the group consisting of: 752±4 cm-1, 1030±4 cm-1, 1046±4 cm-1, 1128±4 cm-1, and 1237±4 cm-1, and generating includes generating an output indicative of the presence of a tumor in the breast tissue.

For some applications, analyzing includes assessing a characteristic of the sample at at least one wavenumber selected from the group consisting of: 797±4 cm-1, 830±4 cm-1, 893±4 cm-1, 899±4 cm-1, 1128±4 cm-1, 1298±4 cm-1, 135±4 cm-1, 1714±4 cm-1 1725±4 cm-1, 1738±4 cm-1, and 3013±4 cm-1, and generating includes generating an output indicative of the presence of a tumor in the gastrointestinal tract tissue.

For some applications, analyzing includes assessing a characteristic of the sample at at least one wavenumber selected from the group consisting of: 765±4 cm-1, 780±4 cm-1, 797±4 cm-1, 851±4 cm-1, 874±4 cm-1, 881±4 cm-1, 913±4 cm-1, 923±4 cm-1, 958±4 cm-1, 968, ±4 cm-1, 1044±4 cm-1, 1085±4 cm-1, 1191±4 cm-1, 1241±4 cm-1, 1344±4 cm-1, 1373±4 cm-1, 1417±4 cm-1, 1458±14 cm-1, 1469±14 cm-1, 1692±4 cm-1, 1714±4 cm-1, 1728±4 cm-1, 2852±4 cm-1, and 2984±4 cm, and generating includes generating an output indicative of the presence of a tumor in the lung tissue.

For some applications, analyzing includes assessing a characteristic of the sample at at least one wavenumber selected from the group consisting of 828±4 cm-1, 932±4 cm-1, 997±4 cm-1, 1059±4 cm-1, 1299±4 cm-1, 1302±4 cm-1, 1403±4 cm-1, 1454±4 cm-1, 1714±4 cm-1, 2979, ±4 cm-1, and 3013±4 cm-1, and generating includes generating an output indicative of the presence of a tumor in the prostate tissue.

There is further provided in accordance with some applications of the present invention a method including:

obtaining an infrared (IR) spectrum of a sample of white blood cells by analyzing the sample by infrared spectroscopy; and based on the infrared spectrum, generating an output indicative of the presence of a solid tumor or a pre-malignant condition.

For some applications, generating the output includes generating the output indicative of the presence of the solid tumor.

For some applications, analyzing the sample by infrared (IR) spectroscopy includes analyzing the sample by Fourier Transformed Infrared (FTIR) spectroscopy, and obtaining the infrared (IR) spectrum includes obtaining a Fourier Transformed Infrared (FTIR) spectrum.

For some applications, analyzing the sample by infrared (IR) spectroscopy includes analyzing the sample by Fourier Transformed Infrared microspectroscopy (FTIR-MSP).

There is additionally provided in accordance with some applications of the present invention a method for monitoring the effect of an anti-cancer treatment on a subject undergoing anti-cancer treatment for a solid tumor, for use with a first Peripheral Blood Mononuclear Cells (PBMC) sample separated from blood of the subject that was obtained prior to initiation of the treatment and a second PBMC sample separated from blood of the subject that was obtained after initiation of the treatment, the method including:

obtaining IR spectra of the first and second PBMC samples by analyzing the first and second PBMC samples by IR spectroscopy and based on the IR spectra, generating an output indicative of the effect of the treatment.

For some applications, analyzing the first and second PBMC samples by IR spectroscopy includes analyzing the samples by Fourier Transformed Infrared spectroscopy, and obtaining the IR spectra includes obtaining Fourier Transformed Infrared (FTIR) spectra.

For some applications, analyzing the first and second PBMC samples by infrared (IR) spectroscopy includes analyzing the first and second PBMC samples by Fourier Transformed Infrared microspectroscopy (FTIR-MSP).

For some applications, the method includes obtaining an IR spectrum of a third PBMC sample separated from blood of the subject that was obtained following termination of the treatment, by analyzing the third PBMC sample by IR spectroscopy.

For some applications, analyzing includes assessing a characteristic of the sample at at least one wavenumber selected from the group consisting of 765±4 cm-1, 798±4 cm-1, 809±4 cm-1, 814±4 cm-1, 875±4 cm-1, 997±4 cm-1, 1001±4 cm-1, 1015±4 cm-1, 1103±4 cm-1, 1118±4 cm-1, 1162±4 cm-1, 1221±4 cm-1, 1270±4 cm-1, 1283±4 cm-1, 1295±4 cm-1, 1315±4 cm-1, 1341±4 cm-1, 1367±4 cm-1, 1392±4 cm-1, 1429±4 cm-1, 1440±4 cm-1, 1445±4 cm-1, and 1455±4 cm-1.

For some applications, analyzing includes assessing the characteristic at at least two wavenumbers selected from the group.

For some applications, analyzing includes assessing the characteristic at at least three wavenumbers selected from the group.

There is yet additionally provided in accordance with some applications of the present invention, a method including:

obtaining an infrared (IR) spectrum of a Peripheral Blood Mononuclear Cells (PBMC) sample by analyzing the sample; and based on the infrared spectrum, generating an output indicative of the presence of a solid tumor or a pre-malignant condition.

For some applications, generating the output includes generating the output indicative of the presence of the solid tumor.

There is still additionally provided in accordance with some applications of the present invention, a system for diagnosing a solid tumor, including:

a data processor, configured to analyze an infrared (IR) spectrum of a Peripheral Blood Mononuclear Cells (PBMC) sample of a subject; and an output unit, configured to generate an output indicative of the presence of a solid tumor, based on the infrared (IR) spectrum.

For some applications, the data processor is configured to calculate a second derivative of the infrared (IR) spectrum of the PBMC sample and, based on the second derivative of the infrared (IR) spectrum, to generate an output indicative of the presence of a solid tumor.

For some applications, the IR spectrum includes a Fourier Transformed Infrared (FTIR) spectrum, and the data processor is configured to calculate a second derivative of the FTIR spectrum.

For some applications, the data processor is configured to analyze the infrared (IR) spectrum by assessing a characteristic of the PBMC sample at at least one wavenumber selected from the group consisting of: 765±4 cm-1, 798±4 cm-1, 809±4 cm-1, 814±4 cm-1, 875±4 cm-1, 997±4 cm-1, 1001±4 cm-1, 1015±4 cm-1, 1103±4 cm-1, 1118±4 cm-1, 1162±4 cm-1, 1221±4 cm-1, 1270±4 cm-1, 1283±4 cm-1, 1295±4 cm-1, 1315±4 cm-1, 1341±4 cm-1, 1367±4 cm-1, 1392±4 cm-1, 1429±4 cm-1, 1440±4 cm-1, 1445±4 cm-1, and 1455±4 cm-1.

For some applications, the data processor is configured to analyze the infrared (IR) spectrum by assessing the characteristic at at least two wavenumbers selected from the group.

For some applications, the data processor is configured to analyze the infrared (IR) spectrum by assessing the characteristic at at least three wavenumbers selected from the group.

There is still further provided in accordance with some applications of the present invention, a computer program product for administering processing of a body of data, the product including a computer-readable medium, having program instructions embodied therein, which instructions, when read by a computer, cause the computer to:

obtain an infrared (IR) spectrum of a Peripheral Blood Mononuclear Cells (PBMC) by analyzing the PBMC by infrared spectroscopy; and based on the infrared spectrum, generate an output indicative of the presence of a solid tumor.

There is yet provided in accordance with some applications of the present invention, a method including:

obtaining an infrared (IR) spectrum of a Peripheral Blood Mononuclear Cells (PBMC) sample by analyzing the sample by infrared spectroscopy; and based on the infrared spectrum, generating an output indicative of the presence of a solid tumor in a breast tissue of a subject.

For some applications, analyzing includes assessing a characteristic of the sample at at least one wavenumber selected from the group consisting of: 752±4 cm-1, 1030±4 cm-1, 1046±4 cm-1, 1128±4 cm-1, and 1237±4 cm-1.

For some applications, analyzing includes assessing the characteristic at at least two wavenumbers selected from the group.

For some applications, analyzing includes assessing the characteristic at at least three wavenumbers selected from the group.

For some applications, analyzing the sample by infrared (IR) spectroscopy includes analyzing the sample by Fourier Transformed Infrared (FTIR) spectroscopy, and obtaining the infrared (IR) spectrum includes obtaining a Fourier Transformed Infrared (FTIR) spectrum.

For some applications, analyzing the sample by infrared (IR) spectroscopy includes analyzing the sample by Fourier Transformed Infrared microspectroscopy (FTIR-MSP).

There is still provided in accordance with some applications of the present invention a method including:

obtaining an infrared (IR) spectrum of a Peripheral Blood Mononuclear Cells (PBMC) sample by analyzing the sample by infrared spectroscopy, and based on the infrared spectrum, generating an output indicative of the presence of a solid tumor in tissue of a gastrointestinal tract of a subject.

For some applications, analyzing includes assessing a characteristic of the sample at at least one wavenumber selected from the group consisting of: 797±4 cm-1, 830±4 cm-1, 893±4 cm-1, 899±4 cm-1, 1128±4 cm-1298±4 cm-1, 1354±4 cm-1, 1714±4 cm-1 1725±4 cm-1, 1738, ±4 cm-1, and 3013±4 cm-1.

For some applications, analyzing includes assessing the characteristic at at least two wavenumbers selected from the group.

For some applications, analyzing includes assessing the characteristic at at least three wavenumbers selected from the group.

For some applications, analyzing the sample by infrared (IR) spectroscopy includes analyzing the sample by Fourier Transformed Infrared (FTIR) spectroscopy, and obtaining the infrared (IR) spectrum includes obtaining a Fourier Transformed Infrared (FTIR) spectrum.

For some applications, analyzing the sample by infrared (IR) spectroscopy includes analyzing the sample by Fourier Transformed Infrared microspectroscopy (FTIR-MSP).

There is additionally provided in accordance with some applications of the present invention, a method including:

obtaining an infrared (IR) spectrum of a Peripheral Blood Mononuclear Cells (PBMC) sample by analyzing the sample by infrared spectroscopy; and based on the infrared spectrum, generating an output indicative of the presence of a solid tumor in lung tissue of a subject.

For some applications, analyzing include assessing a characteristic of the sample at at least one wavenumber selected from the group consisting of: 765±4 cm-1, 780±4 cm-1, 797±4 cm-1, 851±4 cm-1, 874±4 cm-1, 881±4 cm-1, 913±4 cm-1, 923±4 cm-1, 958±4 cm-1, 968, ±4 cm-1, 1044±4 cm-1, 1085±4 cm-1, 1191±4 cm-1, 1241±4 cm-1, 1344±4 cm-1, 1373±4 cm-1, 1417±4 cm-1, 1458±4 cm-1, 1469±4 cm-1, 1692±4 cm-1, 1714±4 cm-1, 1728±4 cm-1, 2852±4 cm-1, and 2984±4 cm.

For some applications, analyzing includes assessing the characteristic at at least two wavenumbers selected from the group.

For some applications, analyzing includes assessing the characteristic at at least three wavenumbers selected from the group.

For some applications, analyzing the sample by infrared (IR) spectroscopy includes analyzing the sample by Fourier Transformed Infrared (FTIR) spectroscopy, and obtaining the infrared (IR) spectrum includes obtaining a Fourier Transformed Infrared (FTIR) spectrum.

For some applications, analyzing the sample by infrared (IR) spectroscopy includes analyzing the sample by Fourier Transformed Infrared microspectroscopy (FTIR-MSP).

There is further additionally provided in accordance with some applications of the present invention, a method including:

obtaining an infrared (IR) spectrum of a Peripheral Blood Mononuclear Cells (PBMC) sample by analyzing the sample by infrared spectroscopy, and based on the infrared spectrum, generating an output indicative of the presence of a solid tumor in a prostate tissue of a subject.

For some applications, analyzing includes assessing a characteristic of the sample at at least one wavenumber selected from the group consisting of: 828±4 cm-1, 932±4 cm-1, 997±14 cm-1, 1059±4 cm-1, 1299±4 cm-1, 1302±4 cm-1, 1403±4 cm-1, 1454±4 cm-1, 1714±4 cm-1, 2979, ±4 cm-1, and 3013±4 cm-1.

For some applications, analyzing includes assessing the characteristic at at least two wavenumbers selected from the group.

For some applications, analyzing includes assessing the characteristic at at least three wavenumbers selected from the group.

For some applications, analyzing the sample by infrared (IR) spectroscopy includes analyzing the sample by Fourier Transformed Infrared (FTIR) spectroscopy, and obtaining the infrared (IR) spectrum includes obtaining a Fourier Transformed Infrared (FTIR) spectrum.

For some applications, analyzing the sample by infrared (IR) spectroscopy includes analyzing the sample by Fourier Transformed Infrared microspectroscopy (FTIR-MSP).

There is further provided in accordance with some applications of the present invention, a method including:

obtaining an infrared (IR) spectrum of a Peripheral Blood Mononuclear Cells (PBMC) sample from a cancer patient by analyzing the sample by infrared spectroscopy, and based on the infrared spectrum, generating an output indicative of a stage of the cancer.

For some applications, analyzing includes assessing a characteristic of the sample at at least one wavenumber selected from the group consisting of: 865±4 cm-1, 897±4 cm-1, 924±4 cm-1, 1030±4 cm-1, 1047±4 cm-1, 1191±4 cm-1, and 1238±4 cm-1.

For some applications, analyzing includes assessing the characteristic at at least two wavenumbers selected from the group.

For some applications, analyzing includes assessing the characteristic at at least three wavenumbers selected from the group.

For some applications, analyzing the sample by infrared (IR) spectroscopy includes analyzing the sample by Fourier Transformed Infrared (FIR) spectroscopy, and obtaining the infrared (IR) spectrum includes obtaining a Fourier Transformed Infrared (FTIR) spectrum.

For some applications, analyzing the sample by infrared (IR) spectroscopy includes analyzing the sample by Fourier Transformed Infrared microspectroscopy (FTIR-MSP).

The present invention will be more fully understood from the following detailed description of embodiments thereof, taken together with the drawings, in which:

BRIEF DESCRIPTION OF THE DRAWINGS

FIGS. 1A-C are graphs representing FTIR absorption spectra and the second derivative of absorption spectra and analysis thereof, based on PBMC samples from several cancer patients and controls, derived in accordance with some applications of the present invention;

FIGS. 2A-C are graphs representing FTIR absorption spectra and the second derivative of absorption spectra of PBMC from a pancreatic cancer patient compared to PBMC from healthy controls, derived in accordance with some applications of the present invention;

FIGS. 3A-C are graphs showing the second derivative of spectra of PBMC from several cancer patients and healthy controls, derived in accordance with some applications of the present invention, and a table summarizing the main biochemical changes induced in PBMC of the cancer patients, as observed by FTIR microspectroscopy, as derived in accordance with some applications of the present invention.

DETAILED DESCRIPTION OF THE EMBODIMENTS

Figure 1A:
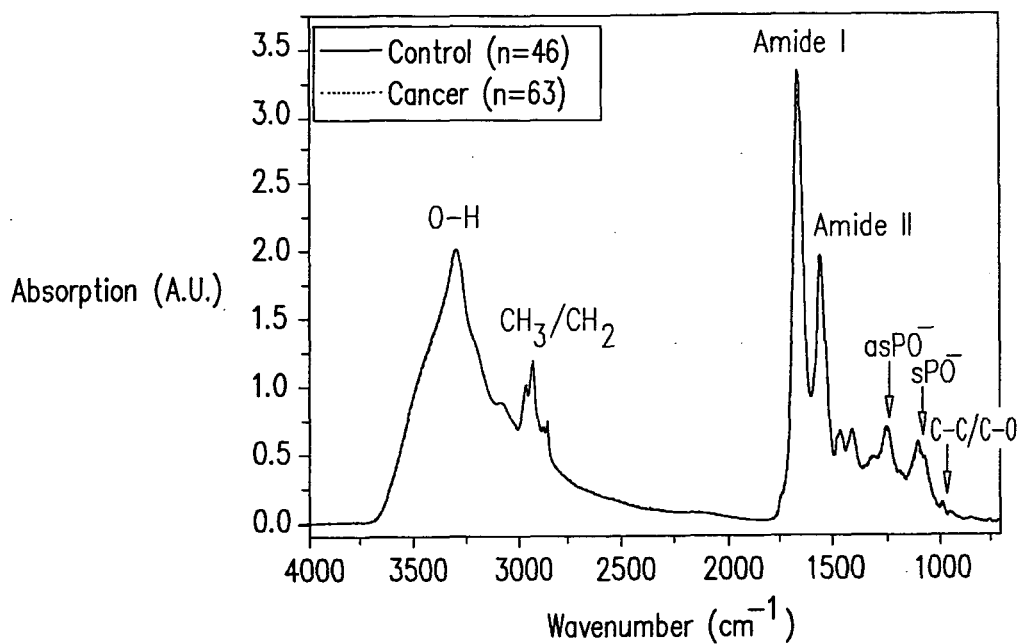

Some applications of the present invention comprise diagnosis of a solid tumor by techniques of IR spectroscopy, e.g., FTIR microspectroscopy (MSP) techniques. For some applications, FTIR Optical Diagnosis Technology (FODT) is used to diagnose a solid tumor based on biochemical proprieties of Peripheral Blood Mononuclear Cells (PBMC) of a subject. Some applications of the present invention comprise obtaining a blood sample from a subject and analyzing mononuclear cells from the sample by FTIR-MSP techniques for the detection of a solid tumor. Typically, a PBMC sample of a patient suffering from a solid tumor is identified as exhibiting FTIR spectra that are different from FTIR spectra produced by PBMC from a subject who does not suffer from a solid tumor (for some applications, the control group may include subjects suffering from a pathology that is not a solid tumor). Accordingly, some applications of the present invention provide a useful method for the detection of cancer, specifically solid tumors. FTIR spectra of PBMC obtained from a cancer patient with a solid tumor generally reflect biochemical changes which occur in the PBMC of the patient in response to the tumor.

For some applications, methods of the present invention are used to determine a stage of the cancer.

For some applications, methods of the present invention can be used to provide monitoring and follow up of cancer patients during and after treatment, e.g., chemotherapy treatment. Typically, changes in FTIR spectra of PBMC of solid-tumor patients who are undergoing treatment can indicate biochemical changes in the cells in response to the treatment. This biochemical information can provide insight into the effect of treatment on the patient and/or the tumor.

In some applications of the present invention, analysis of PBMC by FTIR-MSP is used to detect a type of solid tumor. Typically, each type of malignant solid tumor produces distinct FTIR spectra of the PBMC, which are unique to the type of solid tumor. This can be due to each type of solid tumor inducing specific biochemical changes in PBMC.

Methods Used in Some Embodiments of the Present Invention

A series of protocols are described hereinbelow which may be used separately or in combination, as appropriate, in accordance with applications of the present invention. It is to be appreciated that numerical values are provided by way of illustration and not limitation. Typically, but not necessarily, each value shown is an example selected from a range of values that is within 20% of the value shown. Similarly, although certain steps are described with a high level of specificity, a person of ordinary skill in the art will appreciate that other steps may be performed, mutatis mutandis.

In accordance with some applications of the present invention, the following methods were applied:
Obtaining Patient and Control Populations All studies were approved by the local Ethics Committee of the Soroka University Medical Center and conducted in accordance with the Declaration of Helsinki. Qualified personnel obtained informed consent from each individual participating in this study.

The patient population included cancer patients (n=63) diagnosed with primary solid tumors as set forth in the following Table I:

TABLE I

| | Control | Disease site | | | | |
| | | Breast | GI | Lung | Prostate | Other |
| --- | --- | --- | --- | --- | --- | --- |
| Gender | | | | | | |
| Male | 24 | 1 | 9 | 7 | 5 | 2 |
| Female | 22 | 24 | 9 | 1 | 0 | 5 |
| Disease stage | | | | | | |
| I | 0 | 9 | 1 | 0 | 2 | 2 |
| II | 0 | 12 | 3 | 0 | 0 | 0 |
| III | 0 | 3 | 4 | 1 | 0 | 3 |
| IV | 0 | 1 | 10 | 7 | 3 | 2 |
| Total | 46 | 25 | 18 | 8 | 5 | 7 |

The patient population categorized under "other" included six patients each diagnosed with a different type of primary tumor. Among the "other" group are patients suffering from primary tumors such as pancreas (n=2), head and neck (n=1) and esophagus (n=1).

The diagnosis of cancer was determined by clinical, surgical, histological, and pathologic diagnosis. The pathologic stage of the tumor was determined according to tumor-node-metastasis (TNM) classification, as described in "TNM Classification of Malignant Tumours", by Sobin L H. et al., 7th Edition, New York John Wiley, 2009.

A control group (n=46) included healthy volunteers who underwent detailed clinical questioning to exclude a possible pathology, at the Soroka University Medical Center and Ben-Gurion University.
Collection of Blood Samples 1-2 ml of peripheral blood was collected in 5 ml EDTA blood collection tubes (BD Vacutainer® Tubes, BD Vacutainer, Toronto) from patients and healthy controls using standardized phlebotomy procedures. Samples were processed within two hours of collection.
Extraction of Peripheral Blood Mononuclear Cells (PBMC)

Platelet-depleted residual leukocytes obtained from cancer patients and healthy controls were applied to Histopaque 1077 gradients (Sigma Chemical Co., St Louis, Mo., USA) following manufacturer's protocol to obtain PBMC.

The cells were aspirated from the interface, washed twice with isotonic saline (0.9% NaCl solution) at 250 g, and resuspended in 5 μl fresh isotonic saline. 1.5 μl of washed cells were deposited on zinc selenide (ZnSe) slides to form approximately a monolayer of cells. It is noted that any other suitable slide may be used, e.g., reflection measurements may be carried out using a gold slide. The slides were then air dried for 1 h under laminar flow to remove water. The dried cells were than measured by FTIR microscopy.
FTIR-Microspectroscopy Fourier Transform Infrared Microspectroscopy (FTIR-MSP) and Data Acquisition Measurements on cell cultures were performed using the FTIR microscope IR scope 2 with a liquid-nitrogen-cooled mercury-cadmium-telluride (MCT) detector, coupled to the FTIR spectrometer Bruker Equinox model 55/S, using OPUS software (Bruker Optik GmbH, Ettlingen, Germany). For some of the experiments, Fourier Transform Infrared Microspectroscopy (FTIR-MSP) and Data Acquisition Measurements were performed using the FTIR microscope Nicolet Centaurus with a liquid-nitrogen-cooled mercury-cadmium-telluride (MCT) detector, coupled to the FTIR spectrometer Nicolet iS10, OMNIC software (Nicolet, Madison, Wis.) using OPUS software (Bruker Optik GmbH, Ettlingen, Germany). Essentially the same results were obtained with each of these microscopes.

To achieve high signal-to-noise ratio (SNR), 128 coadded scans were collected in each measurement in the wavenumber region 700 to 4000 $cm^{-1}$. The measurement site was circular with a diameter of 100 μm and a spectral resolution of 4 $cm^{-1}$ (0.482 $cm^{-1}$ data spacing). To reduce cell amount variation and facilitate proper comparison between different samples, the following procedures were adopted.

1. Each sample was measured at least five times at different spots.

2. Analog to Digital Converter (ADC) rates were empirically chosen between 2000 to 3000 counts/sec (providing measurement areas with similar cellular density).

3. The obtained spectra were baseline corrected using the rubber band method, with 64 consecutive points, and normalized using vector normalization in OPUS software as described in an article entitled "Early spectral changes of cellular malignant transformation using Fourier transformation infrared microspectroscopy," by Bogomolny et al, 2007. J Biomed Opt. 12:024003.

In order to obtain precise absorption values at a given wavenumber with minimal background interference, the second derivative spectra were used to determine concentrations of bio-molecules of interest. This method is susceptible to changes in full width at half maximum (FWHM) of the IR bands. However, in the case of biological samples, all cells from the same type are composed from similar basic components which give relatively broad bands. Thus, it is possible to generally neglect the changes in bands FWHM as described in an article entitled "Selenium alters the lipid content and protein profile of rat heart: An FTIR microspectroscopy study," by Toyran et al., Arch. Biochem. Biophys. 2007 458:184-193.

Statistical Analysis:

Statistical analysis was performed using STATISTICA software (STATISTICA, StatSoft, Inc., Tulsa, Okla.) and the student T-test. P-values <0.05 were considered significant.

EXPERIMENTAL DATA

The experiments described hereinbelow were performed by the inventors in accordance with applications of the present invention and using the techniques described hereinabove.

The experiments presented hereinbelow with reference to Example 1 and Example 2 demonstrate that in accordance with some applications of the present invention, analysis of PBMC samples by FTIR-MSP techniques can be used for diagnosis of a solid tumor based on the FTIR-MSP spectral pattern at selected wavenumbers.

Example 1

In a set of experiments, PBMC samples from 46 healthy controls were analyzed by FTIR-MSP, and a typical FTIR-MSP spectral pattern was established for control PBMC. Additionally, PBMC samples from 63 cancer patients suffering from multiple types of solid tumors were subjected to FTIR-MSP analysis and compared to the control FTIR-MSP spectral pattern. The PBMC samples were obtained by preliminary processing of the peripheral blood in accordance with the protocols described hereinabove with reference to extraction of peripheral blood mononuclear cells (PBMC). The PBMC samples were then analyzed by FTIR-MSP, in accordance with the protocols described hereinabove with reference to FTIR-MSP.

Figure 1B:
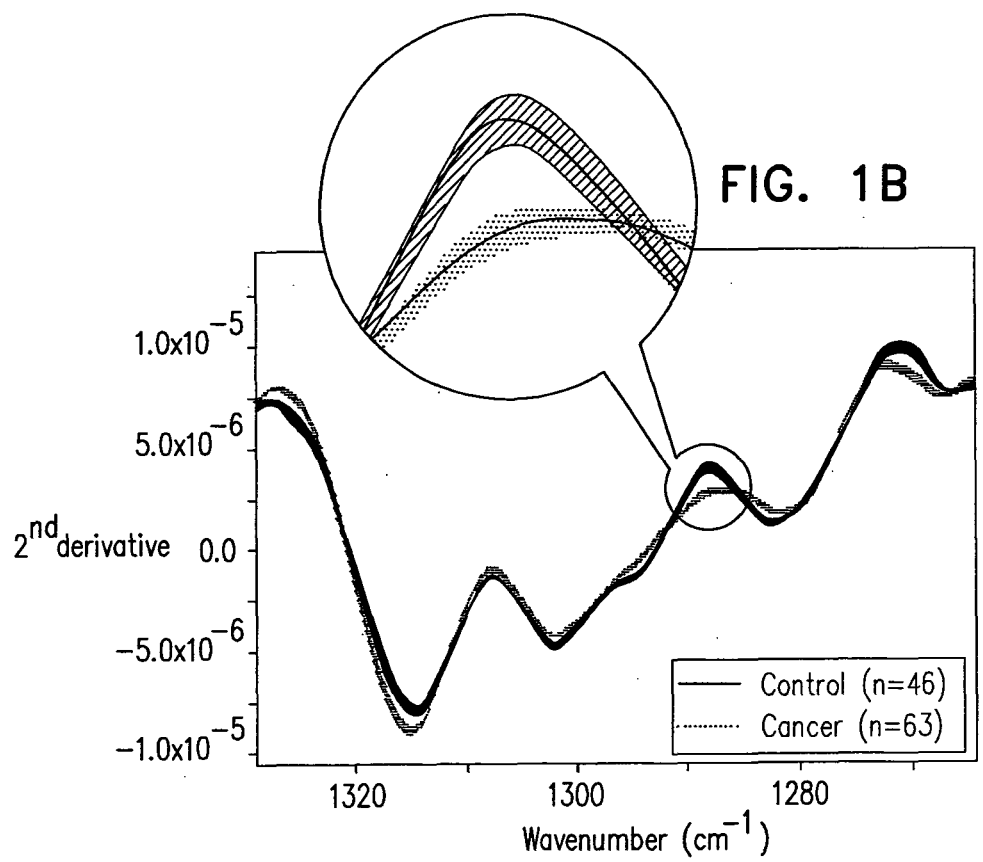

Reference is made to FIGS. 1A-C, which are graphs representing FTIR absorption spectra and the second derivative of the absorption spectra and analysis thereof, for PBMC samples from 63 cancer patients suffering from solid tumors and 46 healthy controls, derived in accordance with some applications of the present invention.

FTIR-MSP analysis of peripheral blood mononuclear cells (PBMC) typically generated spectra in the region of 4000-700 cm-1. The spectra are composed of several absorption bands, each corresponding to specific functional groups of specific macromolecules. FIG. 1A shows an average of the FTIR-MSP spectra of PBMC samples of healthy controls and cancer patients in the regions of 4000-700 cm-1, after baseline correction and vector normalization. The spectra are composed of several absorption bands, each corresponding to specific functional groups of specific macromolecules such as lipids, proteins, and carbohydrates/nucleic acids. The main absorption bands are marked. For example, the region 3000-2830 $cm^{-1}$ contains symmetric and antisymmetric stretching of CH3 and CH2 groups, which correspond mainly to proteins and lipids respectively. The region 1700-1500 cm-1 corresponds to amide I and amide II, which contain information regarding the secondary structures of proteins. The region 1300-1000 cm-1 includes the symmetric and antisymmetric vibrations of PO2-groups. 1000-700 cm-1 is a 'finger print' region which contains several different vibrations, corresponding to carbohydrates, lipids, nucleic acids and other bio-molecules, as described in an article by Mantsch M and Chapman D. entitled "Infrared spectroscopy of bio molecules," John Wiley New York 1996. The FTIR spectrum was typically analyzed by tracking changes in absorption (intensity and/or shift) of these macromolecules.

Table II represents some of the main IR absorption bands for PBMC cells, and their corresponding molecular functional groups:

TABLE II

| Wavenumber (cm-1 ± 4) | Assignment |
| --- | --- |
| 2958 | $v_{as}$ CH$_3$, mostly proteins, lipids |
| 2922 | $v_{as}$ CH$_2$, mostly lipids, proteins |
| 2873 | $v_s$ CH$_3$, mostly proteins, lipids |
| 2854 | $v_s$ CH$_2$, mostly lipids, proteins |
| ~1,656 | Amide I v C=O (80%), v C—N (10%), δ N—H |
| ~1,546 | Amide II δ N—H (60%), v C—N (40%) |
| 1400 | v COO—, δ s CH3 lipids, proteins |
| 1313 | Amide III band components of proteins |
| 1240 | $v_{as}$ PO$_2^-$, phosphodiester groups of nucleic acids |
| 1170 | C—O bands from glycomaterials and proteins |
| 1155 | vC—O of proteins and carbohydrates |
| 1085 | vs PO2— of nucleic acids, phospholipids, proteins |
| 1053 | v C—O & δ C—O of carbohydrates |
| 996 | C—C & C—O of ribose of RNA |
| 967 | C—C & C—O of deoxyribose skeletal motions of DNA |
| 780 | sugar-phosphate Z conformation of DNA |
| 740 | v N=H of Thymine |

Reference is made to FIG. 1B. In order to achieve effective comparison between the PBMC samples of the cancer patients and the controls, the second derivative of the baseline-corrected, vector-normalized FTIR-MSP spectra was used. Results are presented in FIG. 1B. As shown, the second derivative spectra of PBMC samples from the cancer patients differed significantly from the second derivative spectra of PBMC samples from the healthy controls in the spectral region of 1340-1260 cm-1. The mean±SEM is represented by the hashed region (for control) and the dotted region (for cancer) as shown in the exploded view in FIG. 1B.

Reference is made to FIG. 1C, which is a graph representing values of the second derivative of absorption spectra at wavenumbers A1-A23 of PBMC samples from cancer patients compared to PBMC samples from healthy controls, derived in accordance with some applications of the present invention. Statistical analysis was performed and P-values are provided. As shown, the second derivative of PBMC samples from the cancer patients differed significantly from the second derivative analysis of FTIR-MSP spectra from PBMC of healthy controls.

Table III lists the wavenumbers shown in FIG. 1C. Typically, PBMC samples were analyzed by FTIR-MSP techniques using these wavenumbers to distinguish between healthy controls and cancer patients.

TABLE III

Control vs. Cancer

| | Wavenumber (cm-1 ± 4) |
|---|---|
| A1 | 765 |
| A2 | 798 |
| A3 | 809 |
| A4 | 814 |
| A5 | 875 |
| A6 | 997 |
| A7 | 1001 |
| A8 | 1015 |
| A9 | 1103 |
| A10 | 1118 |
| A11 | 1162 |
| A12 | 1221 |
| A13 | 1270 |
| A14 | 1283 |
| A15 | 1295 |
| A16 | 1315 |
| A17 | 1341 |
| A18 | 1367 |
| A19 | 1392 |
| A20 | 1429 |
| A21 | 1440 |
| A22 | 1445 |
| A23 | 1455 |

Example 2

In this set of experiments, PBMC from a single pancreatic cancer patient was subjected to FTIR-MSP analysis and compared to a control FTIR-MSP spectral pattern based on PBMC from 27 healthy controls. Results are presented in FIGS. 2A-C. The PBMC was obtained by preliminary processing of the peripheral blood in accordance with the protocols described hereinabove with reference to extraction of peripheral blood mononuclear cells (PBMC). The PBMC samples were then analyzed by FTIR-MSP in accordance with the protocols described hereinabove with reference to FTIR-Microspectroscopy.

FIG. 2A shows representative FTIR-MSP spectra of PBMC of a healthy control compared to FTIR-MSP spectra of PBMC of a pancreatic cancer patient after baseline correction and Min-Max normalization to amide I. Each spectrum represents the average of five measurements at different sites for each sample. The spectra we composed of several absorption bands, each corresponding to specific functional groups of specific macromolecules such as lipids, proteins, carbohydrates and nucleic acids. The main absorption bends are marked. The FTIR spectrum was analyzed by tracking changes in absorption (intensity and/or shift) of these macromolecules.

As shown in FIG. 2A, the FTIR-MSP spectra derived from analysis of PBMC from the pancreatic cancer patient exhibited a different spectral pattern when compared to the FTIR-MSP spectra of PBMC of healthy controls.

Figure 2C:
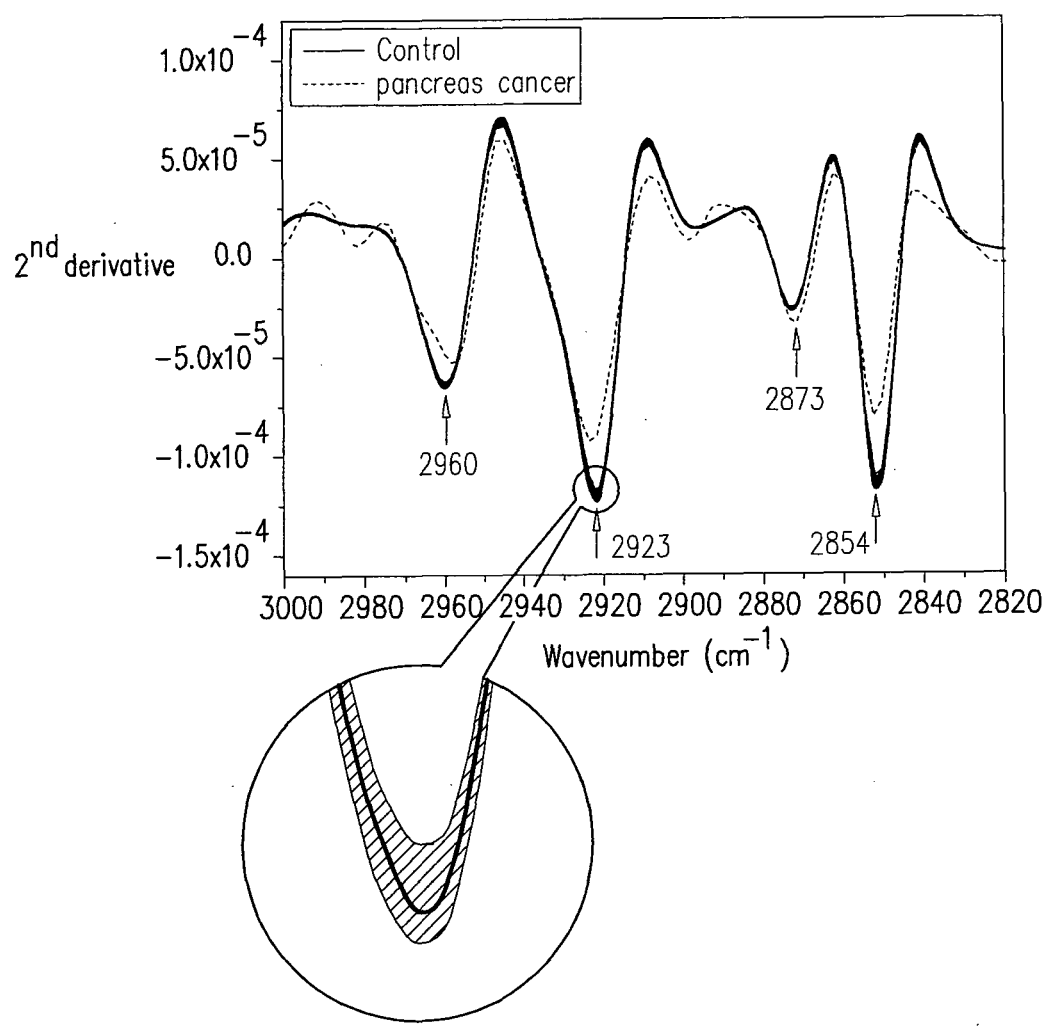

Reference is made to FIGS. 2B-C. In order to increase accuracy and achieve effective comparison between the PBMC sample of the pancreatic cancer patient and healthy controls, the second derivative of the baseline-corrected, vector-normalized FTIR spectra was used. Results are presented in FIGS. 2B-C. The main absorption bands are marked. As shown, the second derivative spectral pattern of PBMC from the pancreatic cancer patient differed significantly from an average FTIR-MSP spectral pattern of PBMC of the healthy controls. The mean±SEM for the controls is represented by the hashed region as shown in the exploded view in FIGS. 2B-C.

Reference is now made to Example 3-Example 5. The experiments presented hereinbelow with reference to Example 3-Example 5 demonstrate that in accordance with some applications of the present invention, analysis of PBMC samples by FTIR-MSP techniques is used to detect a type of solid tumor. Typically, each type of malignant solid tumor produces distinct FTIR spectra of the PBMC which are unique to the type of solid tumor.

Example 3

In this set of preliminary experiments, PBMC from cancer patients suffering from solid tumors, and PBMC from healthy controls was analyzed by FTIR-MSP. The population of cancer patients for this set of experiments comprised a total of 5 patients suffering from the following solid tumors: Breast (n=1), lung (n=1), pancreas (n=1), head and neck (n=1) and esophagus (n=1). The PBMC was obtained by preliminary processing of the peripheral blood in accordance with the protocols described hereinabove with reference to extraction of peripheral blood mononuclear cells (PBMC). The PBMC samples were then analyzed by FTIR-MSP in accordance with the protocols described hereinabove with reference to FTIR-Microspectroscopy.

The results show that the FTIR-MSP spectral pattern of all the cancer patients differs from those of the healthy controls. The results additionally show that each type of malignancy produces a distinct spectral absorption pattern of the PBMC, which is unique to each type of solid tumor.

Reference is made to FIGS. 3A-B. In order to increase accuracy and achieve effective comparison between PBMC samples of cancer patients and healthy controls, the second derivative of the baseline-corrected, vector-normalized FTIR spectra was used. Results are presented in FIG. 3A. As shown in FIG. 3A, the second derivative spectral pattern of PBMC from each one of the cancer patients differed from PBMC of the healthy controls. For example, the FTIR-MSP spectrum of PBMC of the lung cancer patient is distinct from control by exhibiting decreased absorbance of $CH_2$, which corresponds to cellular lipids; a decrease in v, $PO_2^-$; a shift to a higher wavenumber at 967 $cm^{-1}$, which corresponds to deoxyribose skeletal motions of DNA; and an increase in RNA absorption.

Additionally, each spectrum has its own unique spectral pattern, which is distinct from control, and which is characteristic of each type of malignancy.

Reference is made to FIG. 3B, which is a graph showing an analysis of the second derivative data shown in FIG. 3A. FIG. 3B represents the change in value of each type of cancer relative to the control, as derived by analysis by FTIR-MSP of PBMC from each patient. As shown, each cancer patient exhibited a spectrum that differed from the control.

FIG. 3C is a table summarizing the main biochemical changes induced in PBMC of cancer patients suffering from different types of solid tumors, as observed by FTIR-MSP (shown in FIGS. 3A-B) and analyzed in accordance with some applications of the present invention. Peak intensities which indicate absorption were calculated for each spectrum to reveal the main biochemical changes characteristic of each type of tumor.

Example 4

In this set of experiments, PBMC from a breast cancer patient and a gastrointestinal cancer patient were analyzed by FTIR-MSP, and compared to analysis of PBMC from healthy controls. It is to be noted that the breast cancer patient suffers from a primary breast tumor, and the gastrointestinal cancer patient suffers from a primary gastrointestinal tumor. The gastrointestinal cancer patient has a history of breast cancer, and a pathological evaluation of the gastrointestinal tumor showed a breast cancer phenotype rather than a gastrointestinal phenotype.

First, peripheral blood was extracted from the two cancer patients and 27 healthy controls. The PBMC was obtained by preliminary processing of the peripheral blood in accordance with the protocols described hereinabove with reference to extraction of peripheral blood mononuclear cells (PBMC). The PBMC samples were then analyzed by FTIR-MSP in accordance with the protocols described hereinabove with reference to FTIR-Microspectroscopy.

The results show that the FTIR-MSP spectral pattern of PBMC from the cancer patients differs significantly from those of the healthy controls. The results additionally show that PBMC of the breast cancer patient and the gastrointestinal cancer patient (with a history of breast cancer) exhibited a similar spectral pattern that was distinct from the control. This can be explained by the gastrointestinal tumor being shown by pathological evaluation to have a phenotype characteristic of a breast tumor. In some cases of breast cancer, malignant cells break away from the primary breast tumor and spread to other parts of the body. These cells may remain inactive for years before they begin to grow again. It is possible that a tumor, although located remotely from the original tumor site, triggers biochemical changes in the PBMC that are similar to those triggered by the original tumor. It is to be noted that the spectral absorbance pattern of PBMC of both the breast cancer patient and the gastrointestinal cancer patient (who has a history of breast cancer) differ from the spectral pattern produced by PBMC of patients suffering from other types of solid tumors.

Figure 4:
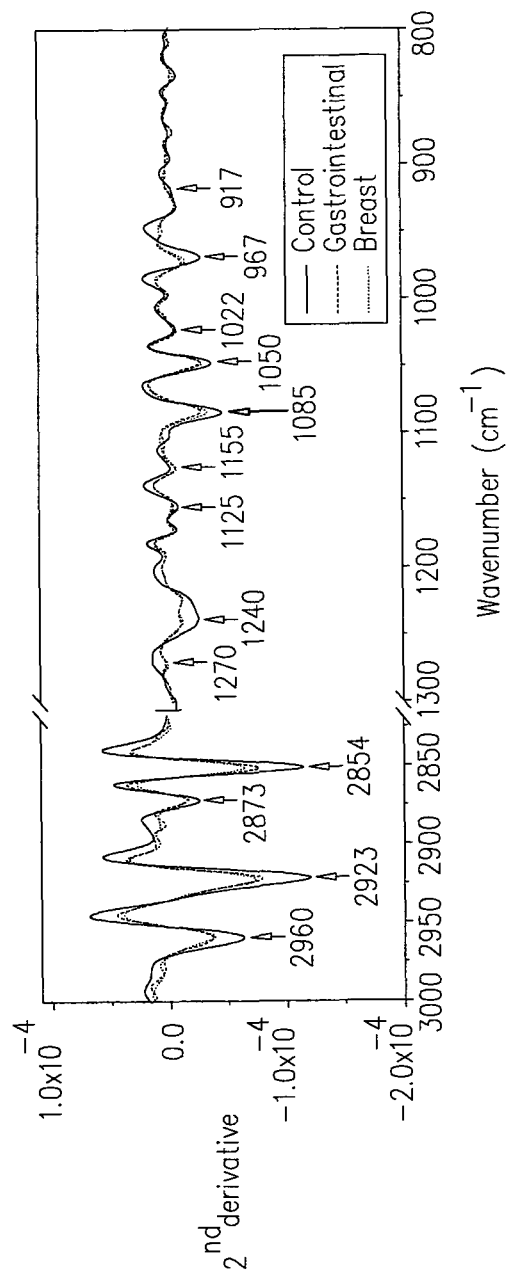
FIG. 4 shows second derivative spectra of PBMC from a breast cancer patient, a gastrointestinal cancer patient with a history of breast cancer, and healthy controls, as derived in accordance with some applications of the present invention.

FIG. 4 shows second derivative spectra of PBMC from the breast cancer patient and from the gastrointestinal cancer patient (the gastrointestinal cancer patient having a history of breast cancer and the gastrointestinal tumor exhibiting a phenotype characteristic of a breast tumor) compared to PBMC of healthy controls, as derived in accordance with some applications of the present invention. As shown, the FIR-MSP second derivative spectra exhibit significant differences between PBMC from the cancer patients and PBMC from healthy controls. These spectral differences typically represent molecular changes in the PBMC of the cancer patients and allow distinguishing between the healthy control and the cancer patients. In addition, PBMC from both the primary breast cancer patient and the gastrointestinal cancer patient exhibited a similar FTIR-MSP spectral pattern. Accordingly, some applications of the present invention can be used to diagnose the type and/or the origin of solid tumor of a patient based on the unique FTIR-MSP spectra produced by analysis of the patient's PBMC. This is consistent with Example 3, which showed that PBMC from patients with different types of solid tumors each produced a distinct FTIR spectral pattern with its own set of characteristic bands. Additionally, the molecular changes which trigger the changes in the FTIR-MSP spectra of breast cancer patients, including patients with breast cancer history, can serve as biomarkers to diagnose breast cancer. Additionally, some applications of the present invention can be used to select effective treatment based on the origin of a tumor. It is to be noted that the type of solid tumor diagnosed in accordance with applications of the present invention is not limited to breast tumors, but may include any other type of solid tumors.

Example 5

In this set of experiments, PBMC samples from cancer patients suffering from various types of solid tumors were analyzed by FTIR-MSP. The FTIR-MSP spectral pattern of each type of solid tumor was compared to the FTIR-MSP spectral pattern of the other solid tumors, allowing distinguishing between different types of solid tumors. The population of cancer patients for this set of experiments comprised a total of 63 patients suffering from solid rumors, in accordance with Table I. The PBMC was obtained by preliminary processing of the peripheral blood in accordance with the protocols described hereinabove with reference to extraction of peripheral blood mononuclear cells (PBMC). The PBMC samples were then analyzed by FTIR-MSP, in accordance with the protocols described hereinabove with reference to FTIR-Microspectroscopy.

The results show that each type of solid tumor produces a distinct spectral absorption pattern of the PBMC, which is unique to each type of solid tumor, allowing distinguishing between different types of solid tumors.

Figure 5A:
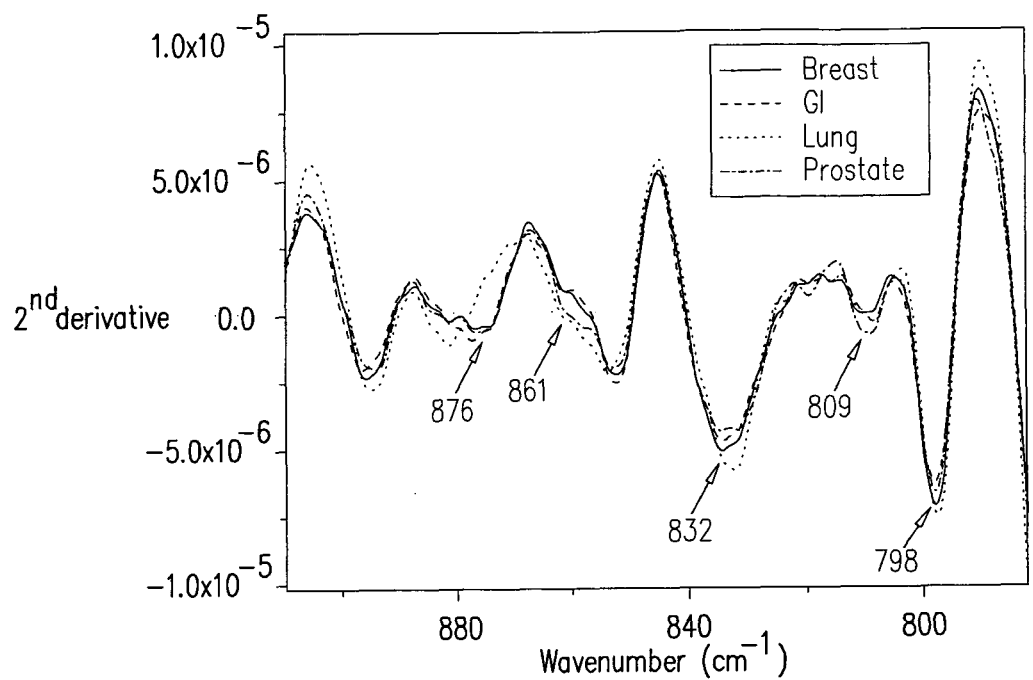
FIGS. 5A-G are graphs representing the second derivative spectra of PBMC and analysis thereof, based on PBMC samples from cancer patients suffering from various types of solid tumors, derived in accordance with some applications of the present invention.
Figure 5B:
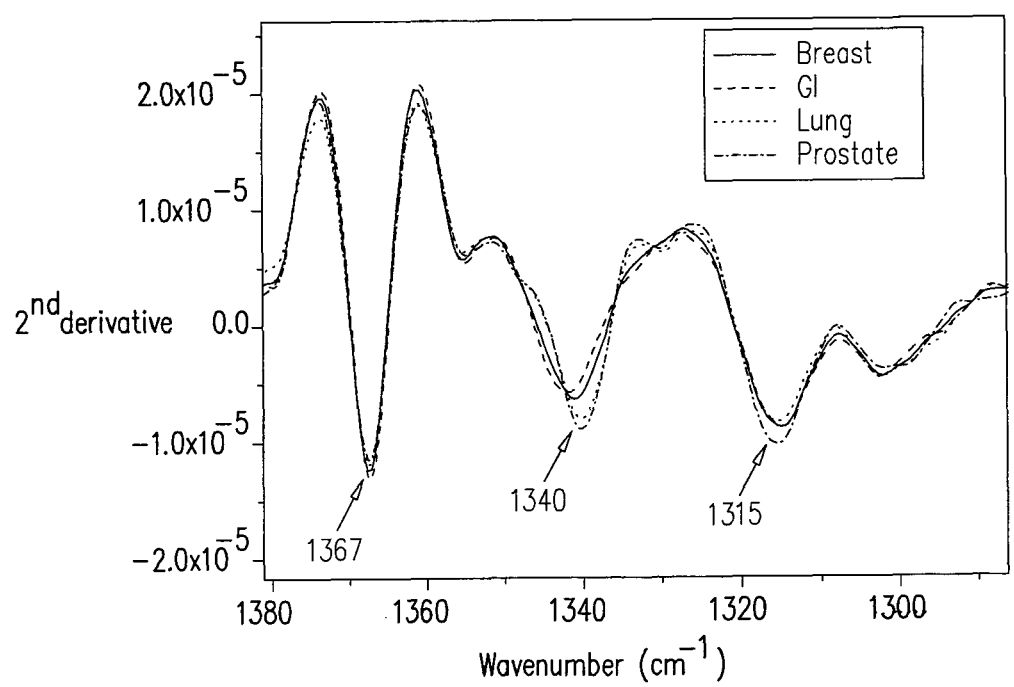
Figure 5C:
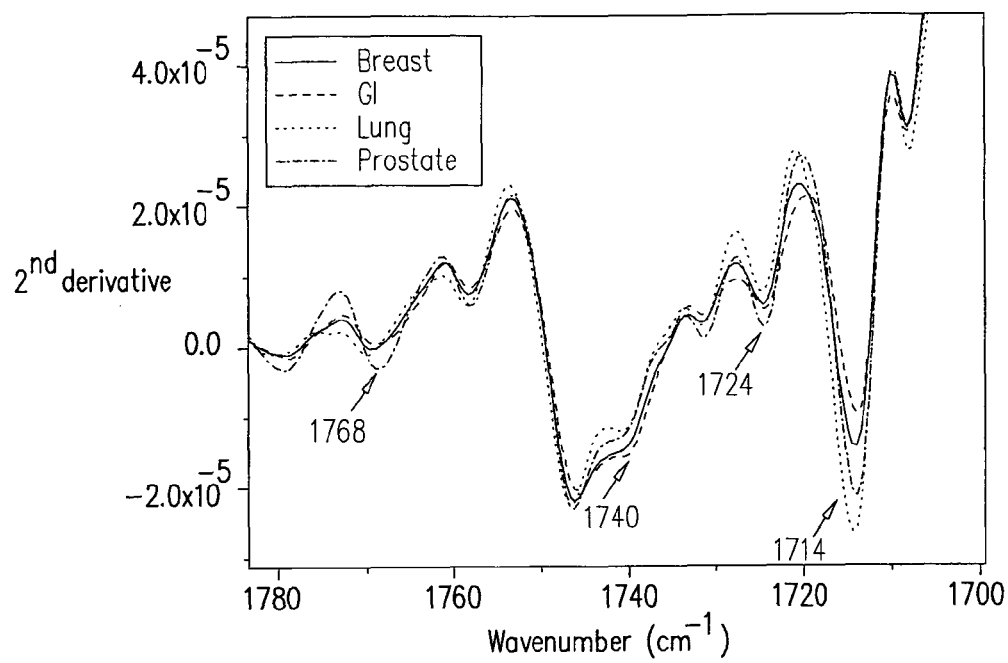

Reference is made to FIGS. 5A-C. In order to increase accuracy and achieve effective comparison between PBMC samples of the various types of cancer patients, the second derivative of the baseline-corrected, vector-normalized average FTIR absorption spectra was used. Results are presented in FIGS. 5A-C, showing the second derivative of several regions of the spectra (the main absorption bends are marked). As shown in FIGS. 5A-C, the second derivative spectra of each type of solid tumor produced a distinct spectral absorption pattern of the PBMC, which is unique to each type of solid tumor.

Reference is made to FIGS. 5D-G, which are a series of graphs representing values of the second derivative of absorption spectra of each type of solid tumor compared to the second derivative of absorption spectra of the other solid tumors, derived in accordance with some applications of the present invention.

Figure 5D:
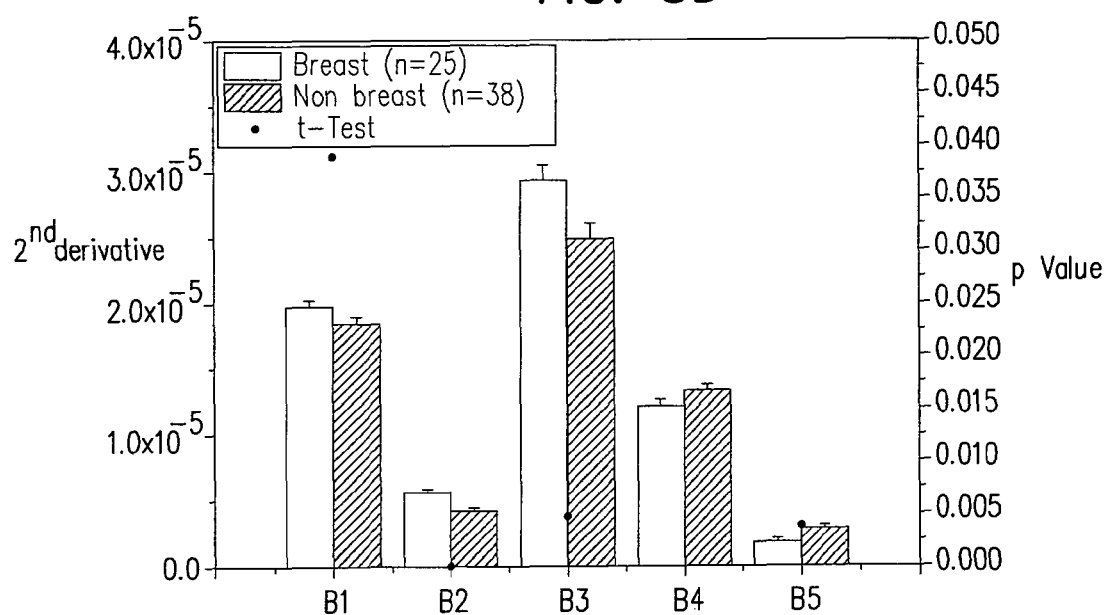

FIG. 5D is a graph representing values of the second derivative of absorption spectra of PBMC samples from the breast cancer patients (n=25) compared to PBMC samples from the cancer patients suffering from other types of solid tumors that do not include breast cancer (n=38), at wavenumbers B1-B5. Statistical analysis was performed and P-values are provided. As shown, the second derivative of PBMC from the breast cancer patients differed significantly from the second derivative analysis of FTIR-MSP spectral patterns from PBMC of other cancer patients who do not have breast cancer.

Table IV lists the wavenumbers shown in FIG. 5D. Typically, PBMC samples were analyzed by FTIR-MSP techniques using these wavenumbers to distinguish between breast cancer patients and cancer patients who do not have breast cancer.

TABLE IV

| Breast vs. Non Breast | |
|---|---|
| | Wavenumber (cm−1 ± 4) |
| B1 | 752 |
| B2 | 1030 |
| B3 | 1046 |
| B4 | 1128 |
| B5 | 1237 |

Figure 5E:
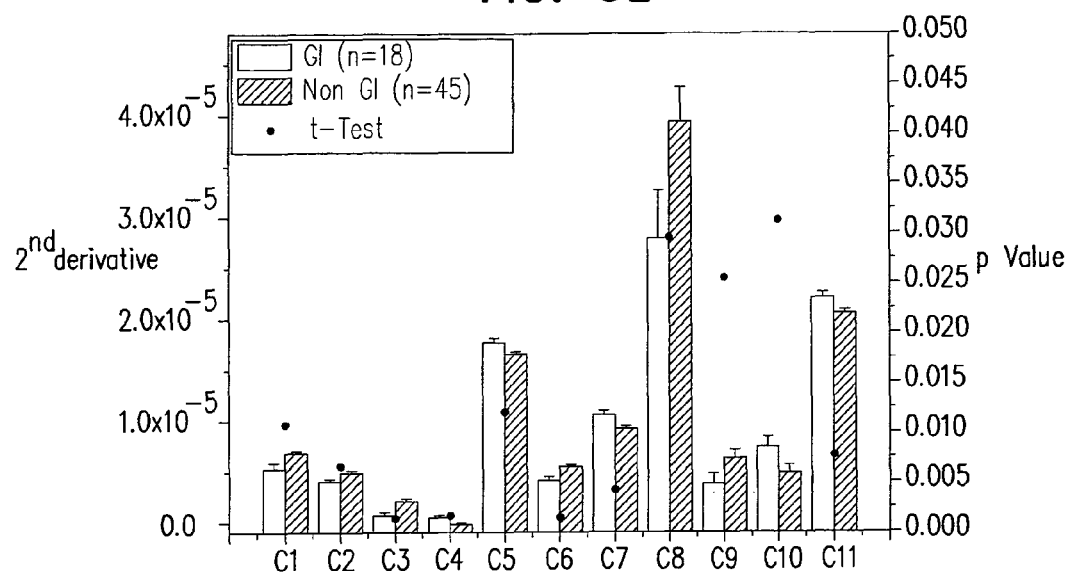

FIG. 5E is a graph representing values of the second derivative of absorption spectra of PBMC samples from the gastrointestinal cancer patients (n=18) compared to PBMC samples from the cancer patients suffering from other types of solid tumors that do not include gastrointestinal tumors (n=45), at wavenumbers C1-C11. Statistical analysis was performed and P-values are provided. As shown, the second derivative of PBMC from the gastrointestinal cancer patients differed significantly from the second derivative analysis of FTIR-MSP spectral pattern from PBMC of other cancer patients who do not have gastrointestinal cancer.

Table V lists the wavenumbers shown in FIG. 5E. Typically, PBMC samples were analyzed by FTIR-MSP techniques using these wavenumbers to distinguish between gastrointestinal cancer patients and cancer patients who do not have gastrointestinal cancer.

TABLE V

| GI vs. Non GI | |
|---|---|
| | Wavenumber (cm−1 ± 4) |
| C1 | 797 |
| C2 | 830 |
| C3 | 893 |
| C4 | 899 |
| C5 | 1128 |
| C6 | 1298 |
| C7 | 1354 |
| C8 | 1714 |
| C9 | 1725 |
| C10 | 1738 |
| C11 | 3013 |

Figure 5F:
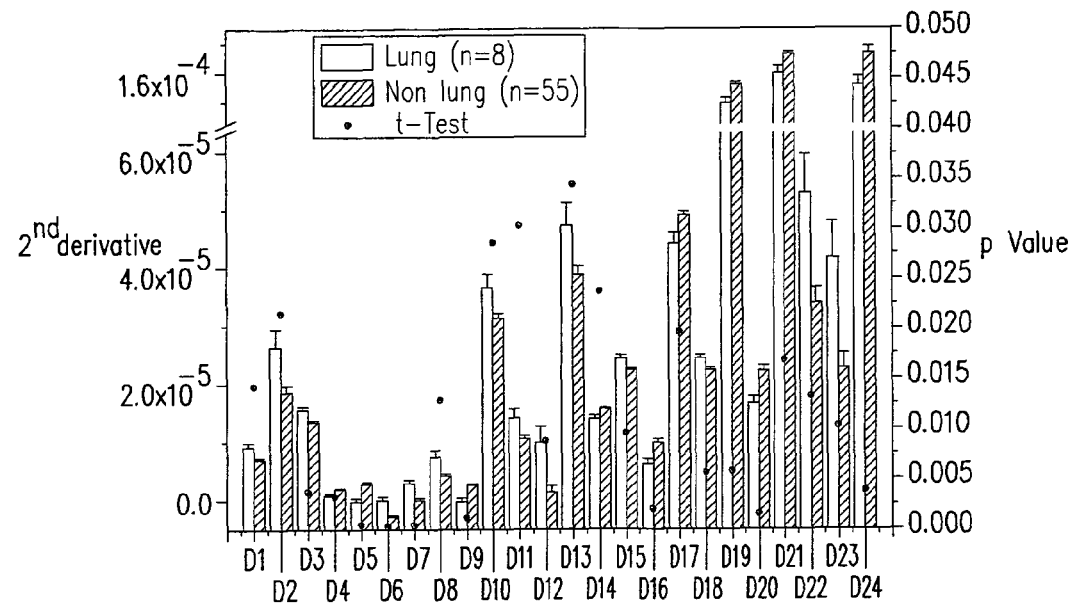

FIG. 5F is a graph representing values of the second derivative of absorption spectra of PBMC samples from the lung cancer patients (n=8) compared to PBMC samples from the cancer patients suffering from other types of solid tumors that do not include lung tumors (n=55) at wavenumbers D1-D24. Statistical analysis was performed and P-values are provided. As shown, the second derivative of PBMC from the lung cancer patients differed significantly from the second derivative analysis of FTIR-MSP spectral patterns from PBMC of other cancer patients who do not have lung cancer.

Table VI lists the wavenumbers shown in FIG. 5F. Typically, PBMC samples were analyzed by FTIR-MSP techniques using these wavenumbers to distinguish between lung cancer patients and cancer patients who do not have lung cancer.

TABLE VI

| Lung vs. Non Lung | |
|---|---|
| | Wavenumber (cm−1 ± 4) |
| D1 | 765 |
| D2 | 780 |
| D3 | 797 |
| D4 | 851 |
| D5 | 874 |
| D6 | 881 |
| D7 | 913 |
| D8 | 923 |
| D9 | 958 |
| D10 | 968 |
| D11 | 1044 |
| D12 | 1085 |
| D13 | 1191 |
| D14 | 1241 |
| D15 | 1344 |
| D16 | 1373 |
| D17 | 1417 |
| D18 | 1458 |
| D19 | 1469 |
| D20 | 1692 |
| D21 | 1714 |
| D22 | 1728 |
| D23 | 2852 |
| D24 | 2984 |

Figure 5G:
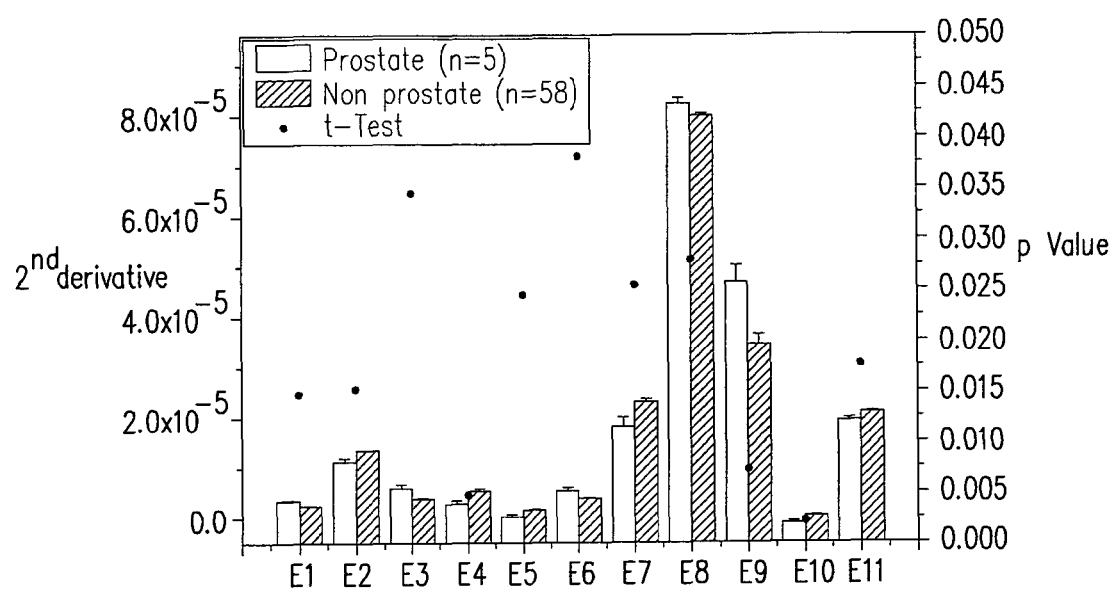

FIG. 5G is a graph representing values of the second derivative of absorption spectra of PBMC samples from the prostate cancer patients (n=5) compared to PBMC samples from the cancer patients suffering from other types of solid tumors that do not include prostate cancer (n=58) at wavenumbers E1-E11. Statistical analysis was performed and P-values are provided. As shown, the second derivative of PBMC from the prostate cancer patients differed significantly from the second derivative analysis of FTIR-MSP spectral pattern from PBMC of other cancer patients who do not have prostate cancer.

Table VII lists the wavenumbers shown in FIG. 5G. Typically, PBMC samples were analyzed by FTIR-MSP techniques using these wavenumbers to distinguish between prostate cancer patients and cancer patients who do not have prostate cancer.

TABLE VII

| Prostate vs. Non Prostate | |
|---|---|
| | Wavenumber (cm−1 ± 4) |
| E1 | 828 |
| E2 | 932 |
| E3 | 997 |
| E4 | 1059 |
| E5 | 1299 |
| E6 | 1302 |
| E7 | 1403 |
| E8 | 1454 |
| E9 | 1714 |
| E10 | 2979 |
| E11 | 3013 |

Reference is now made to Example 6. The experiments presented hereinbelow with reference to Example 6 demonstrate that in accordance with some applications of the present invention, analysis of PBMC samples by FTIR-MSP techniques is used for staging cancer. Typically, each stage of cancer produces distinct FTIR spectra of the PBMC.

Example 6

In this set of experiments, PBMC samples from cancer patients suffering from different stages of cancer due to solid tumors were analyzed by FTIR-MSP and a second derivative of the average of the spectra was obtained for each of the stages of cancer, allowing distinguishing between different stages of cancer. The population of cancer patients for this set of experiments comprised a total of 63 patients suffering from the different stages (stages one and two (n=29), and stages three and four (n=34)) of cancer, as described in Table I.

The PBMC was obtained by preliminary processing of the peripheral blood in accordance with the protocols described hereinabove with reference to extraction of peripheral blood mononuclear cells (PBMC). The PBMC samples were then analyzed by FTIR-MSP in accordance with the protocols described hereinabove with reference to FTIR-Microspectroscopy.

The results show that early stages of cancer produce spectral absorption pattern of the PBMC, that are different than those produced by PBMC samples taken from patients with advanced stages of cancer, allowing distinguishing among different stages of cancer, in particular, between early and advanced stages.

Figure 6A:
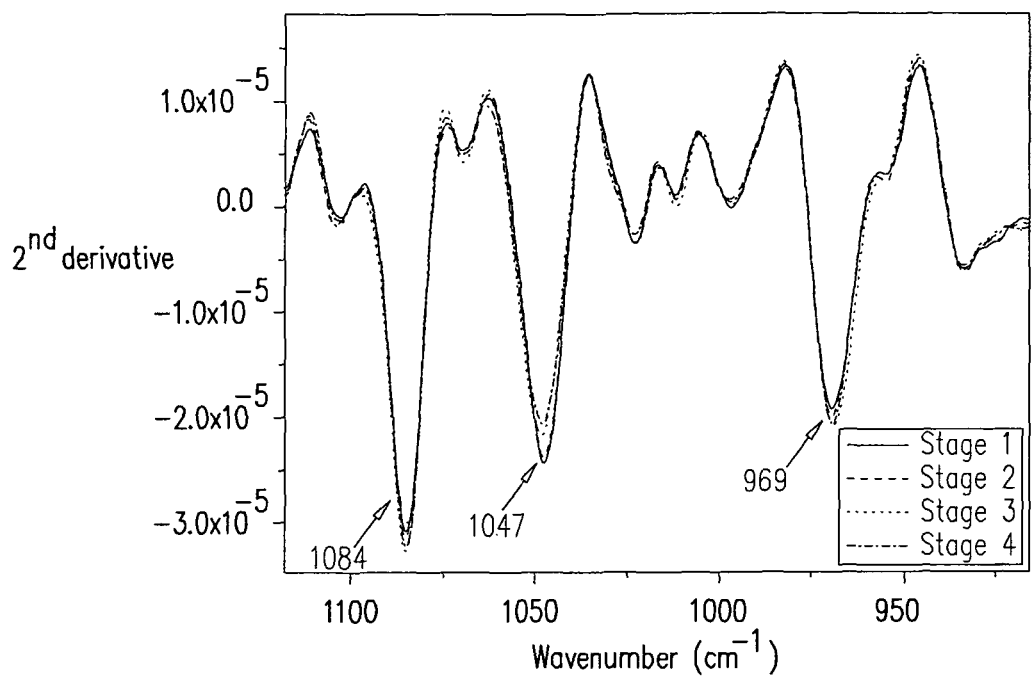
FIGS. 6A-C are graphs representing the second derivative spectra and analysis thereof, of PBMC samples from cancer patients suffering from different stages of cancer, derived in accordance with some applications of the present invention.
Figure 6B:
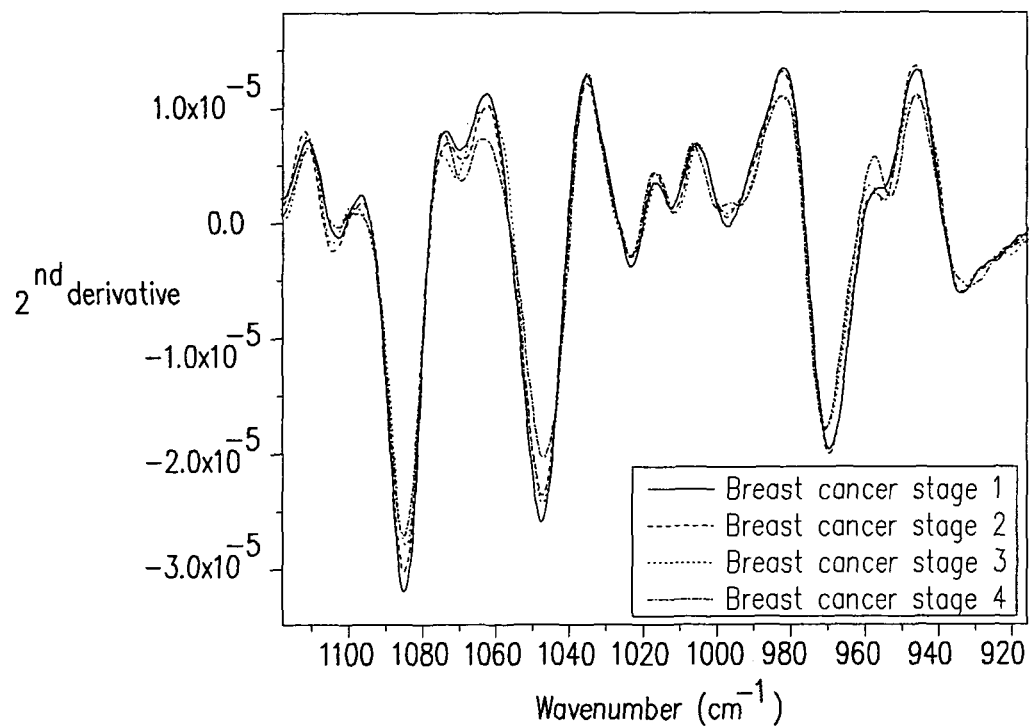
Figure 6C:
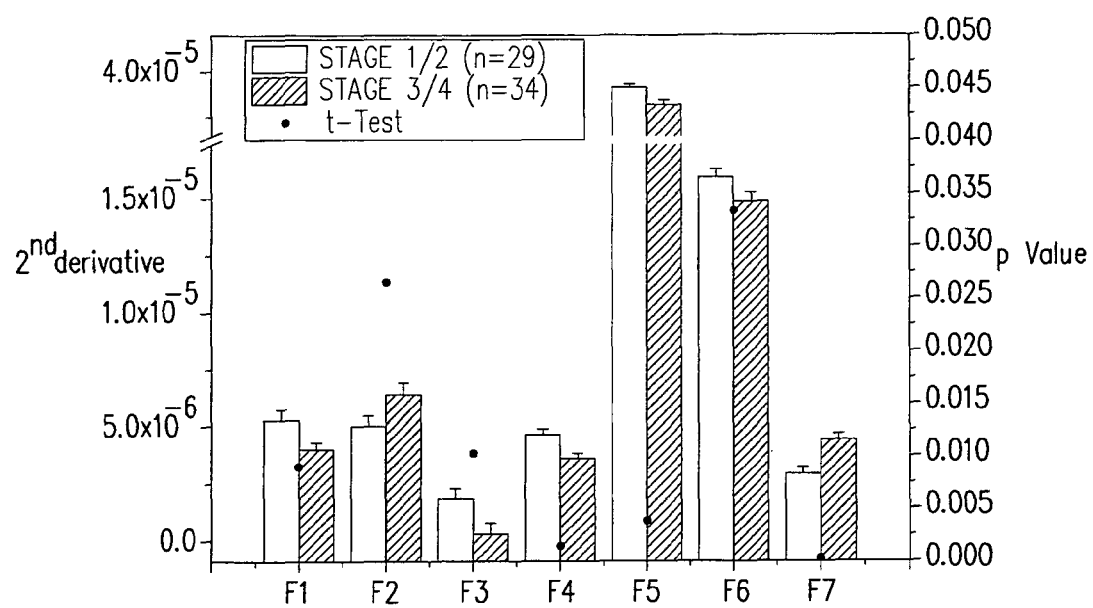

Reference is made to FIGS. 6A-C, which are graphs showing the second derivative spectra of PBMC and analysis thereof based on PBMC samples from cancer patients suffering from different stages of cancer, derived in accordance with some applications of the present invention.

FIG. 6A is a graph representing the second derivative of baseline-corrected, vector-normalized average FTIR absorption spectra of PBMC samples obtained from cancer patients in different stages of the disease. As shown, PBMC of each stage of cancer produced a distinct spectral absorption pattern of the PBMC.

FIG. 6B is a graph representing the second derivative of baseline-corrected, vector-normalized average FTIR absorption spectra of PBMC samples obtained from breast cancer patients in different stages of the disease. As shown, PBMC of each stage of breast cancer produced a distinct spectral absorption pattern of the PBMC, and particularly, the early stages (stages one and two) were distinct from the more advanced stages (stages three and four). It is to be noted that breast cancer is shown by way of illustration and not limitation, and that the scope of the present includes staging of any type of solid tumor by techniques described herein.

FIG. 6C is a graph representing values of the second derivative of absorption spectra of PBMC samples from stage one and two (n=29) cancer patients, compared to stage three and four (n=34) cancer patients at wavenumbers F1-F7. Statistical analysis was performed and P-values are provided. As shown, the second derivative of PBMC from the cancer patients with early stages of cancer (stages one and two) differed significantly from the second derivative analysis of FTIR-MSP spectral pattern of cancer patients with advanced stages of cancer (stage three and four).

Table VIII lists the wavenumbers shown in FIG. 6A. Typically, PBMC samples were analyzed by FTIR-MSP techniques using these wavenumbers to distinguish between early stages (stage one and two) and more advanced stages (three and four) of cancer.

TABLE VIII

Initial Stages vs. Advanced Stages

| | Wavenumber (cm-1 ± 4) |
|---|---|
| F1 | 865 |
| F2 | 897 |
| F3 | 924 |
| F4 | 1030 |
| F5 | 1047 |
| F6 | 1191 |
| F7 | 1238 |

Reference is made to FIGS. 1-6 and Examples 1-6. It is to be noted that techniques described herein with reference to use of peripheral blood mononuclear cells (PBMC) may be applied to any type of white blood cell (WBC) or a combination of types of white blood cells. For example, analysis by FTIR microscopy techniques may be performed on any type of white blood cell, including but not limited to a total population of white blood cells (e.g., as obtained by red blood cell lysis).

Reference is still made to FIGS. 1-6 and Examples 1-6.

The data obtained by analysis of the PBMC samples may be further analyzed by any suitable method known in the art, e.g., Artificial Neural Network and/or Cluster Analysis, and/or Principal Component Analysis, and/or Linear Discriminant Analysis (LDA) e.g., Fisher's Linear Discriminant Analysis (FLDA), Quadratic Discriminant Analysis, and/or Non Linear Discriminant Analysis.

For example, data obtained in accordance with applications of the present invention may be analyzed by an artificial neural network (ANN). Several biomarkers shown in Tables II-VII which are statistically significant ($p<0.05$) may be served as an input vector for the ANN analysts.

It is further noted that the scope of the present invention includes the use of only one wavenumber (representing one biomarker) for detection and/or monitoring of a solid tumor, as well as the use of two, three, four, or more wavenumbers.

Additionally, the scope of the present invention includes using any IR spectral feature or any feature derived from analysis of an IR spectral feature (e.g., any type of peak analysis), to indicate the presence of a solid tumor.

It is also noted that the scope of the present invention is not limited to any particular form or analysis of IR spectroscopy. For example, IR spectroscopy may include Attenuated Total Reflectance (ATR) spectroscopy techniques.

Although applications of the present invention are described hereinabove with respect to spectroscopy, microspectroscopy, and particularly FTIR spectroscopy, the scope of the present invention includes the use of analysis techniques with data obtained by other means as well (for example, using a monochromator or an LED, at specific single wavenumbers, and/or FTIR imaging).

It will additionally be understood by one skilled in the art that aspects of the present invention described hereinabove can be embodied in a computer running software, and that the software can be supplied and stored in tangible media, e.g., hard disks, floppy disks, a USB flash drive, or compact disks, or in intangible media, e.g., in an electronic memory, or on a network such as the Internet.

It will be appreciated by persons skilled in the art that the present invention is not limited to what has been particularly shown and described hereinabove. Rather, the scope of the present invention includes both combinations and subcombination of the various features described hereinabove, as well as variations and modifications thereof that are not in the prior art, which would occur to persons skilled in the art upon reading the foregoing description.

The invention claimed is:

1. A method comprising:
   identifying that a subject may have a solid tumor in breast tissue;
   in response to the identifying, obtaining a Fourier Transformed infrared (FTIR) spectrum of a Peripheral Blood Mononuclear Cells (PBMC) sample of the subject by analyzing the sample by Fourier Transformed Infrared (FTIR) spectroscopy and assessing a characteristic of the sample of the subject at the wavenumbers: 1015±4 cm-1, 1162±4 cm-1, 1221±4 cm-1, and 1270±4 cm-1; and
   using a data processor, comparing, at the wavenumbers, the infrared spectrum to an infrared spectrum obtained from a PBMC sample from a person without a solid tumor, to detect a difference between the infrared spectrum of the PBMC sample of the subject and the infrared spectrum obtained from the PBMC sample from the person without a solid tumor.

2. The method according to claim 1, wherein analyzing the sample by infrared (IR) spectroscopy comprises analyzing the sample by Fourier Transformed Infrared microspectroscopy (FTIR-MSP).

3. The method according to claim 1, wherein assessing the characteristic further comprises assessing a characteristic of the sample of the subject at at least one wavenumber selected from the group consisting of: 765±4 cm-1, 798±4 cm-1, 809±4 cm-1, 814±4 cm-1, 875±4 cm-1, 997±4 cm-1, 1001±4 cm-1, 1103±4 cm-1, 1118±4 cm-1, 1283±4 cm-1, 1295±4 cm-1, 1315±4 cm-1, 1341±4 cm-1, 1367±4 cm-1, 1392±4 cm-1, 1429±4 cm-1, 1440±4 cm-1, 1445±4 cm-1 and 1455±4 cm-1.

4. The method according to claim 1, wherein assessing the characteristic comprises analyzing a band of the IR spectrum of the PBMC sample of the subject surrounding at least one wavenumber.

5. The method according to claim 1, wherein analyzing the sample comprises obtaining a second derivative of the infrared (IR) spectrum of the sample of the subject.

6. The method according to claim 1, wherein the infrared (IR) spectrum of the PBMC sample of the subject includes an absorption spectrum, and wherein obtaining the infrared (IR) spectrum comprises obtaining the absorption spectrum.

7. The method according to claim 1, wherein assessing the characteristic further comprises assessing a characteristic of the sample of the PBMC sample of the subject at at least one wavenumber selected from the group consisting of: 752±4 cm-1, 1030±4 cm-1, 1046±4 cm-1, 1128±4 cm-1, and 1237±4 cm-1.

8. The method according to claim 1, wherein assessing the characteristic further comprises assessing a characteristic of the sample of the subject at at least one wavenumber selected from the group consisting of: 765±4 cm-1, 997±4 cm-1, 1001±4 cm-1, 1103±4 cm-1, 1118±4 cm-1, 1283±4 cm-1, 1341±4 cm-1, 1367±4 cm-1, 1392±4 cm-1, 1440±4 cm-1, 1445±4 cm-1 and 1455±4 cm-1.

9. The method according to claim 1, further comprising treating the subject with anti-cancer treatment.

* * * * *